United States Patent
Anand et al.

(10) Patent No.: US 12,369,814 B1
(45) Date of Patent: Jul. 29, 2025

(54) METHODS AND SYSTEMS FOR DETERMINING POSITION SIGNALS OF ELECTRODES USING A RETRAINED MACHINE-LEARNING MODEL

(71) Applicant: Anumana, Inc., Cambridge, MA (US)

(72) Inventors: Deepak Anand, Doddanekundi (IN); Yogisha Heggadahalli Jayendra, Bengaluru (IN); Karthik K. Bharadwaj, Bengaluru (IN); Sughosh Indurkar, Bangalore (IN); Rakesh Barve, Bengaluru (IN); Animesh Agarwal, San Francisco, CA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/920,266

(22) Filed: Oct. 18, 2024

(51) Int. Cl.
*A61B 5/06* (2006.01)
*A61B 5/00* (2006.01)
*A61B 5/367* (2021.01)
*A61M 25/01* (2006.01)

(52) U.S. Cl.
CPC .............. *A61B 5/068* (2013.01); *A61B 5/062* (2013.01); *A61B 5/6852* (2013.01); *A61B 5/7267* (2013.01); *A61B 5/367* (2021.01); *A61B 5/7264* (2013.01); *A61M 25/0127* (2013.01); *A61M 2025/0166* (2013.01)

(58) Field of Classification Search
CPC ....... A61B 5/068; A61B 5/062; A61B 5/6852; A61B 5/36; A61B 5/7264; A61B 5/7267; A61B 5/367; G06N 3/09; A61M 25/0127; A61M 2025/0166
See application file for complete search history.

(56) References Cited

U.S. PATENT DOCUMENTS

| | | | |
|---|---|---|---|
| 7,536,218 B2 | 5/2009 | Govari et al. | |
| 9,345,405 B2 | 5/2016 | Everling et al. | |
| 10,614,373 B1* | 4/2020 | Jeffery | G06N 5/04 |
| 11,317,966 B2 | 5/2022 | Gliner et al. | |
| 2017/0330075 A1* | 11/2017 | Tuysuzoglu | G06N 7/08 |

(Continued)

FOREIGN PATENT DOCUMENTS

| | | | | |
|---|---|---|---|---|
| CN | 110968826 A | 4/2020 | | |
| CN | 111345909 A | 6/2020 | | |
| CN | 114403900 A | * 4/2022 | ............. | A61B 5/259 |

*Primary Examiner* — Tung S Lau
(74) *Attorney, Agent, or Firm* — Caldwell Intellectual Property Law

(57) ABSTRACT

A system for determining position signals of electrodes using a retrained machine-learning model includes at least a catheter including a plurality of electrodes configured to collect a plurality of potential signals and a magnetic sensor configured to collect magnetic data, and at least a computing device including a memory. The processor receives a first training set, wherein the first training set includes patient-agnostic data; receives a second training set, wherein the second training set includes patient-specific data, trains a mapping machine-learning model using the first training set, retrains the mapping machine-learning model using the second training set, receives at least a first signal, wherein the first signal includes a potential signal of the plurality of potential signal and the magnetic data, and generates, using the retrained machine-learning model, as a function of the at least a first signal, a first position signal for an electrode of the plurality of electrodes.

20 Claims, 28 Drawing Sheets

(56) References Cited

U.S. PATENT DOCUMENTS

| | | | |
|---|---|---|---|
| 2019/0228547 A1* | 7/2019 | Chandarana | G06N 3/048 |
| 2020/0138334 A1* | 5/2020 | Hill | A61B 5/6852 |
| 2022/0039882 A1* | 2/2022 | Botzer | G16H 50/20 |
| 2023/0089504 A1* | 3/2023 | Khanna | G06V 10/771 |
| | | | 706/20 |
| 2023/0377751 A1* | 11/2023 | Somani | G16H 50/20 |
| 2023/0386184 A1* | 11/2023 | Duffy | G06N 3/09 |

\* cited by examiner

Run2:

METHODS AND SYSTEMS FOR DETERMINING POSITION SIGNALS OF ELECTRODES USING A RETRAINED MACHINE-LEARNING MODEL

FIELD OF THE INVENTION

The present invention generally relates to the field of electro-anatomical mapping. In particular, the present invention is directed to methods and systems for determining position signals of electrodes using a retrained machine-learning model.

BACKGROUND

Current electro-anatomical mapping systems face challenges in accurately detecting magnetic and impedance signals across different subjects. During medical procedures, variations between subjects often lead to inaccurate impedance and cardiac calibrations. Existing solutions struggle to adjust localization models for precise sensor positioning.

SUMMARY OF THE DISCLOSURE

In an aspect, a system for determining position signals of electrodes using a retrained machine-learning model includes at least a catheter including a plurality of electrodes configured to collect a plurality of potential signals and a magnetic sensor configured to collect magnetic data, and at least a computing device including a memory. The memory contains instructions configuring the processor to receive a first training set, wherein the first training set includes patient-agnostic data; receive a second training set, wherein the second training set includes patient-specific data, train a mapping machine-learning model using the first training set, retrain the mapping machine-learning model using the second training set, receive at least a first signal, wherein the first signal includes a potential signal of the plurality of potential signal and the magnetic data, and generate, using the retrained machine-learning model, as a function of the at least a first signal, a first position signal for an electrode of the plurality of electrodes.

In another aspect, a method for determining position signals of electrodes using a retrained machine-learning model includes receiving, by at least a processor, a first training set, wherein the first training set comprises patient-agnostic data, receiving, by the at least a processor, a second training set, wherein the second training set comprises patient-specific data, training, by the at least a processor, a mapping machine-learning model using the at least a first training set, retraining, by the at least a processor, the mapping machine-learning model using the at least a second training set, receiving, by at least a catheter, at least a first signal, wherein the first signal comprises a potential signal of the plurality of potential signal and the magnetic data; and generating, by the at least a processor, using the retrained machine-learning model, as a function of the at least a first signal, a first position signal for an electrode of the plurality of electrodes.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for determining position signals of electrodes using a retrained machine-learning model. The apparatus for determining position signals of electrodes using a retrained machine-learning model includes at least a catheter including a plurality of electrodes configured to collect a plurality of potential signals and a magnetic sensor configured to collect magnetic data, and at least a computing device including a memory. The memory contains instructions configuring the processor to receive a first training set, wherein the first training set includes patient-agnostic data; receive a second training set, wherein the second training set includes patient-specific data, train a mapping machine-learning model using the first training set, retrain the mapping machine-learning model using the second training set, receive at least a first signal, wherein the first signal includes a potential signal of the plurality of potential signal and the magnetic data, and generate, using the retrained machine-learning model, as a function of the at least a first signal, a first position signal for an electrode of the plurality of electrodes.

Figure 1:
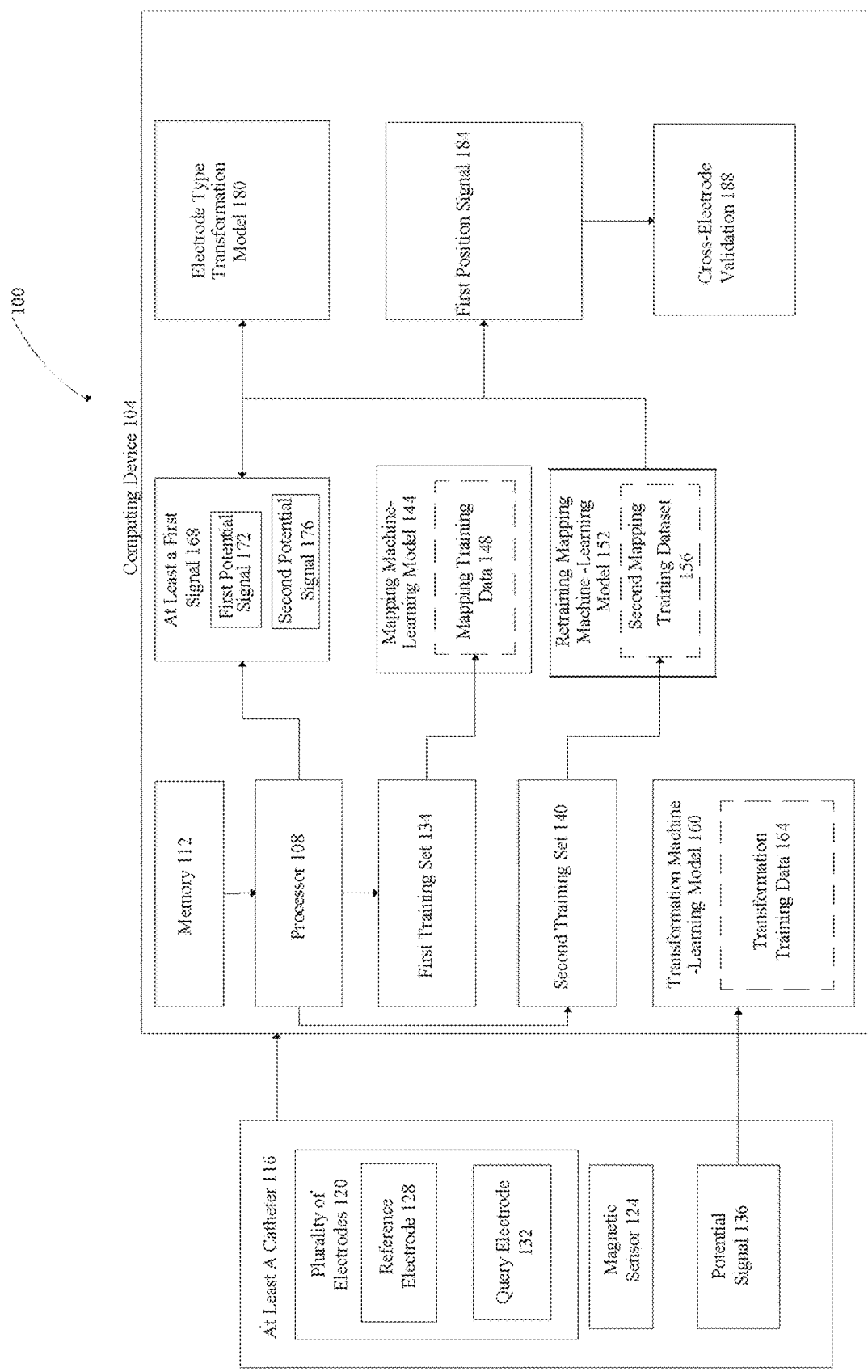
FIG. 1 is a block diagram of a particular implementation of a system for determining position signals of electrodes using a retrained machine-learning model.

Referring now to FIG. 1, an exemplary embodiment of a system for determining position signals of electrodes using a retrained machine-learning model is illustrated. System 100 includes a computing device 104. Computing device 104 includes a processor 108 communicatively connected to a memory 112. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting Computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented, as a non-limiting example, using a "shared nothing" architecture.

With continued reference to FIG. 1, Computing device 104 may be designed and/or configured to perform any method, method step, or sequence of method steps in any embodiment described in this disclosure, in any order and with any degree of repetition. For instance, Computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, memory 112 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power.

"Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 108 may access the information from primary memory.

Still referring to FIG. 1, system 100 includes at least a Catheter 116 including a Plurality of Electrodes 120. As used herein, a "catheter" refers to a flexible, tube-like medical device that is used for various diagnostic and therapeutic procedures within the body. At least a Catheter 116 may include at least a tip that is configured to interact directly with body tissues or systems during medical procedures. At least a Catheter 116 may include a Plurality of Electrodes 120. In this disclosure, the term "electrode" refers to a multi-functional component used for both diagnostic and therapeutic purposes in medical procedures. Electrodes may include conductive elements for delivering targeted treatments, such as ablation within the body, while also serving diagnostic functions. This dual role is essential in procedures like cardiac ablation, where accurately locating and treating abnormal electrical pathways is critical. In an embodiment, a location of the plurality of electrodes may be computed as a function of at least the magnetic sensor 124 and rigid inter-electrode distances. In an embodiment, the plurality of electrodes may include a reference electrode 128 located on the rigid portion of the at least a Catheter 116. A "reference electrode" refers to an electrode for which the position is known. The rigid portion of the at least a Catheter 116 may refer to the part of the catheter that does not bend or flex. In another embodiment, the plurality of electrodes may include a query electrode 132 located on a flexible portion of the catheter. A "query electrode" refers to an electrode whose position is being determined. The "flexible portion" of the at least a Catheter 116 may allow the electrodes to move and adapt to contours of a patient. In an embodiment, the reference electrode 128 and query electrode 132 may be different types of electrodes. For instance, reference electrode 128 may be a surface electrode, such as an ECG electrode, Silver, Silver Chloride Electrode, and the like. Query electrode 132 may be an electrode placed inside of an patient, such as a mapping electrode or other type of flexible electrode used to gather electrical data in complex anatomical areas. At least a Catheter 116 comprises a plurality of electrodes configured to collect a plurality of potential signals. Collecting a plurality of potential signals refers to gathering multiple electrical signals, specifically voltage differences or electrical potentials, from various sources or locations surrounding the at least a catheter. The plurality of potential signals 136 may include various types of signals such as voltage, current, potential, resistance, impedance, electrochemical, bioelectrical, and magnetoelectric signals, among others. These signals may have characteristics like amplitude, frequency, and/or phase. Additionally, the plurality of potential signals 136 can encompass data from at least a reference electrode 128 and a query electrode 132, where the data includes the types of signals and their characteristics discussed in relation to signal. As used herein, a "potential signal" is a signal conveying the electrical potential difference between an electrode and a reference electrode. Throughout this disclosure, the terms "reference electrode" and "query electrode" are used in connection with the plurality of potential signals 136, as described above, and in the context of one or more applications of system 100. At least a Catheter 116 is configured to detect and record several electrical signals at once from the plurality of electrodes to analyze or map the electrical activity within a patient or saline tank. The at least a Catheter 116 may include a magnetic sensor configured to collect magnetic data. As used herein, a "magnetic sensor" refers to a device integrated into the at least a catheter configured to detect magnetic fields and use the detected information to determine the at least a catheter's precise location and orientation inside the patient or saline tank. Such sensors may determine the strength, direction and/or in some embodiments the rate of change of a magnetic field. Exemplary embodiments of magnetic sensor 124 may include magnetoresistive sensors, hall effect sensors, fluxgate sensors, magnetic resonance imaging (MRI)-compatible sensors, and/or the like. Position data may include spatial coordinates, orientation, distance, alignment, and/or the like. Further, spatial coordinates may include x, y, z coordinates in three-dimensional space and/or polar coordinates for spherical or cylindrical setups. Orientation may include the angle and/or positioning of the electrode in relation to other components or the medium with which it is interacting with. Position data may also include quaternions. Quaternions may be used to track an object's attitude. Quaternions are a mathematical system used to represent rotations in 3D space. In some embodiments, position data may include an attitude of the magnetic sensor including quaternions $Q_0$, $Q_1$, $Q_2$, and $Q_3$. They consist of one real part and three imaginary parts, often written as $q=w+xi+yj+zk$, where w,x,y,z are real numbers, and i,j,k are the imaginary units. For example, and without limitation, the angle of inclination or rotation relative to a reference plane. Further, distance may be measured from a fixed point or other reference electrode 128. For example, the distance from a reference electrode 128 and/or the distance from the magnetic sensor 124.

Figure 2:
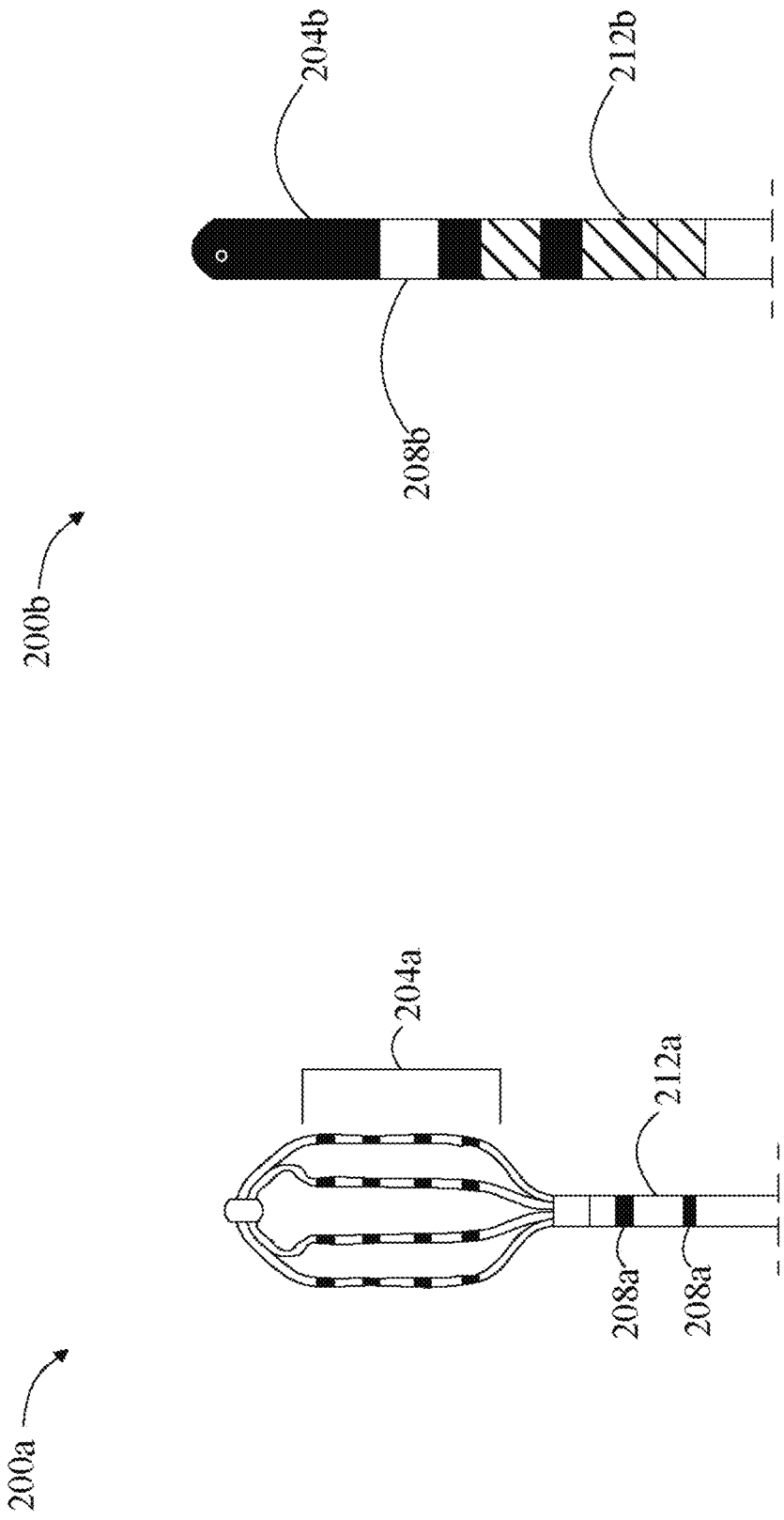
FIG. 2A-B is a diagram illustrating an exemplary embodiment of a catheter with electrodes in a grid orientation.

In further reference to FIG. 1, in an embodiment, the Plurality of Electrodes 120 may include one or more rigid electrodes and one or more flexible electrodes. Rigid electrodes may yield reference electrode 128. Whereas flexible electrodes may yield at least a query electrode 132. As used throughout this disclosure, a "rigid electrode" is a type of electrode that maintains a fixed, inflexible shape during its operation. Unlike flexible or deformable electrodes, rigid electrodes are designed to stay in constant position and structure. For example, a rigid electrode may include metal electrodes, carbon-based electrodes, ceramic electrodes, conductive polymers, and/or reference electrode 128. Each of these examples has its own advantages and/or disadvantages and may be chosen based on its specific application. As used throughout this disclosure, a "flexible electrode" is an electrode designed to bend, stretch, and/or conform to various surfaces without losing its functionality. For example, flexible electrodes may include conductive polymers, metal mesh or foil electrodes, carbon-based flexible electrodes, hydrogels, and/or stretchable elastomers with conductive fillers. These electrodes may be used in place of and/or in combination with rigid electrodes for certain applications. Flexible electrodes may adapt to different shapes and movements, making them ideal for dynamic and/or complex environments. Advantages of flexible electrodes may include flexibility, conformability, durability, and conductivity. In one or more embodiments, system 100 implements at least a Catheter 116 including both one or more rigid electrodes and/or one or more flexible electrodes. In some embodiments, the plurality of electrodes 120 may be orientated in a grid-like fashion. In such an embodiment, the plurality of electrodes 120 may be located in a grid, wherein each electrode is 1 mm in length and spaced 3 mm apart from one another. Additionally, in such an embodiment there may be one or more shaft electrodes located on either side of magnetic sensor 124. For example, and without limitation, like the Tacticath catheter. For a more detailed description of such an embodiment, further disclosure may be found with reference to FIG. 2A. Alternatively, in some embodiments, one or more electrodes may be orientated in a straight-line orientation. For example, and without limitation, like the HDGrid 18-electrode catheter with two types of electrodes. For a more detailed description of such an embodiment, further disclosure may be found with reference to FIG. 2B.

Still referring to FIG. 1, system 100 may include at least a localization system configured to detect at least a position signal as a function of a location of the at least a transducer. As used in this disclosure, a "localization system" is a specialized apparatus designed to detect and determine the position of a catheter within a body or environment by utilizing position signal. These signals are a function of at least a Catheter 116 location, enabling precise tracking and navigation during medical procedures. In a non-limiting example, the purpose of at least a localization system is to enhance the safety and efficacy of catheter-based interventions by providing critical spatial information. As used in this disclosure, a "position signal" is a signal generated by localization system to determine the location of a catheter within the body. With continued reference to FIG. 1, in a non-limiting example, localization system may be consistent with one or more aspects of the localization system described in U.S. patent application Ser. No. 18/764,853, filed on Jul. 5, 2024, titled "SYSTEM AND METHOD FOR LOCATING A MEDICAL DEVICE USING AN ELECTRICAL FIELD CREATION," which is incorporated by reference herein in its entirety.

With continued reference to FIG. 1, at least a localization system may include one or more of an electromagnetic localization system, and an impedance-based localization system. As used in this disclosure, an "electromagnetic localization system" is a type of localization technology that uses electromagnetic fields to determine the precise position and orientation of objects within a given space. This system typically involves generating a low-frequency electromagnetic field in the area of interest, and then tracking the position of sensors or coils that respond to this field. The sensors may be integrated into catheters or other medical instruments, allowing for accurate real-time tracking of their location and movement within the body. In the context of electroanatomic mapping, the electromagnetic localization system enables the precise localization of at least a Catheter 116 tip within the heart. This is achieved by placing electromagnetic field generators around the patient and using sensors on at least a Catheter 116 to detect the field. The system calculates the exact position and orientation of at least a Catheter 116 by measuring the electromagnetic field's strength and direction at the sensor's location. This information is then transmitted to the processor, which uses it to construct a detailed, three-dimensional map of the heart's anatomy. This technology is essential for guiding medical procedures such as catheter ablation, where precise navigation within the heart is critical. By providing accurate and real-time positional data, the electromagnetic localization system ensures that at least a Catheter 116 can be maneuvered safely and effectively to target areas of abnormal electrical activity, thereby improving the outcomes of the procedure.

With continued reference to FIG. 1, as used in this disclosure, "impedance-based localization system" is a technique used to determine the position of a catheter or other medical device within the body by measuring the electrical impedance at electrodes placed on the patient's body. This method may involve passing a small, alternating current through the body and measuring the resulting voltage at different points, allowing the system to calculate the impedance. At least a localization system can then use these impedance measurements to triangulate the exact position of at least a Catheter 116 tip within the heart or other body cavities. Impedance varies with the distance and the type of tissue between at least a Catheter 116 and the electrodes, enabling precise tracking of the device's location. This technique is particularly useful in electroanatomic mapping and other procedures requiring accurate real-time positioning of medical instruments within the body.H In a non-limiting example, system 100 may employ other tracking technologies, such as optical localization system or impedance-based localization, to generate position signal. Optical localization system uses cameras and reflective markers on at least a Catheter 116 to capture its movement and position, while impedance-based localization measures electrical impedance differences between at least a Catheter 116 and the body tissues. These methods provide accurate real-time spatial information that processor 108 uses alongside the potential signal.

With continued reference to FIG. 1, at least a processor 108 may be configured to receive at least a first training set 134. As used herein, a "first training set" refers to a dataset information containing patient-agnostic data. "Patient-agnostic data" refers to data that is collected, processed, or used in a way that is independent of the individual characteristics of a specific patient. Patient-agnostic data may be generalized and applied across different patients, regardless of variations in anatomy, physiology or medical history. Patient-agnostic data may refer to models, algorithms, or datasets that are designed to work effectively for any patients, without needing customization for individual differences. Patient-agnostic data may allow system 100 to operate or make predictions based on general principles rather than being tailored to a specific patient. In a non-limiting embodiment, examples of patient-agnostic data may include catheter calibration data, tissue ablation protocols, electrode placement, mapping data, electrical impedance data, signal processing algorithms, catheter positioning, navigation models, magnetic field data, force sensing data, and the like. In an embodiment, first training set 134 may include exemplary magnetic data, exemplary reference electrode potential signals, exemplary reference electrode position signals, and exemplary query electrode potential signals correlated to exemplary query electrode position signals. In an embodiment, the first training set may include automatically collected data from a saline tank, featuring extensive variations in electrode placement, salinity levels, and different solid models within the tank. Saline tank data refers to data collected from experiments or tests conducted in a tank filled with a saline solution. Saline tanks are often used to test medical devices, for example electrodes or sensors used in electro-anatomical mapping, cardiac procedures, or neural research are placed in saline tanks to observe how they function in a conductive environment similar to a living organism's tissue. Medical devices, such as the at least a Catheter 116 described herein, may be tested in saline tanks to measure how well they detect electrical or magnetic signals, to ensure or measure accuracy before being used on living organisms. A saline tank can be used to test devices by controlling variations in salinity and electrode placement, allowing researchers to observe how these factors influence signal conduction and device performance.

With continued reference to FIG. 1, at least a processor may be configured to receive a second training set 140 including patient-specific data. As used herein, "patient-specific data" refers to information that is unique to an individual patient. In a non-limiting embodiment, patient-specific data may include anatomical data, electrophysiological data, medical history, genetic or biomarker data, real-time physiological data, and the like. The second training set may comprise 10% randomly sampled patient-specific data. In another non-limiting embodiment, the second training set may include 90% patient-specific data.

With continued reference to FIG. 1, at least a processor 108 may be configured to train a mapping machine-learning model 144 using mapping training data. In an embodiment, the mapping machine-learning model is configured to determine position signals for electrodes as a function of magnetic information and potential signals; In an embodiment, mapping training data 148 includes the first training set 134. The mapping machine-learning model 144 is configured to predict the query electrode 132 location given a magnetic sensor data, a voltage of the reference electrode 128, the location of the reference node, and a voltage of the query electrode 132. The mapping machine-learning model may be trained using the first training set 134 wherein the first training set comprises inputs such as magnetic sensor data, voltage of a reference electrode 128, potential signal of a reference electrode 128, location of the reference electrode 128, voltage of the query electrode 132, correlated to outputs such as the location of a query electrode 132. The mapping machine-learning model may be trained used previous iterations of outputs of query electrode 132 locations as inputs. The mapping machine-learning model may use historical inputs of magnetic sensor data, voltage of a reference electrode 128, location of the reference electrode 128, potential signal of a reference electrode 128, voltage of the query electrodes 132 to generate outputs of query electrode 132 locations. The mapping machine-learning model may use examples of inputs as training data. The mapping machine-learning model 144 may be formulated with a supervised deep learning model, which may be implemented in accordance with FIGS. 4-6. In an embodiment, the inputs of magnetic sensor data, voltage of a reference electrode 128, location of the reference electrode 128, voltage of the query electrode 132 have known locations, while the output of the voltage of the query electrode 132 is within a 30-millimeter radius of the known locations.

Continuing to refer to FIG. 1, at least a processor 108 may use user feedback to train the model described above. In some embodiments, if user feedback indicates that an output of the machine-learning model was "bad," then that output and the corresponding input may be removed from training data used to train the machine-learning model, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of mapping machine-learning model 144 may include user feedback.

With continued reference to FIG. 1, in some embodiments, an accuracy score may be calculated for mapping machine-learning model 144 using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons and used as described above. Accuracy score or another score as described above may indicate a degree of retraining needed for a machine-learning model such as a classifier; computing device 104 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

With continued reference to FIG. 1, at least a processor 108 may be configured to retrain the mapping machine-learning model 144 using a second mapping training data set 156. In a non-limiting embodiment, a second mapping training data set includes second training set 140. In an embodiment, the second training set 140 is used to retrain the mapping machine-learning model 144 previously trained using the first training set. Retraining 156 the mapping machine-learning model 144 using the second training set 140 may result in outputting a location of the query electrode 132 for a patient using the patient specific-data. Retraining the mapping machine-learning model 144 using the second training set 140 may include retraining the mapping machine-learning model using single shot learning. As used herein, "single shot learning" refers to a machine leaning technique that enables a model to learn to recognize or classify new categories based on one or very few examples. Single shot learning differs from traditional machine-learning techniques by focusing on the ability to generalize from minimal data rather than requiring large datasets for training. In an embodiment, single shot learning may require only a single example, such as the second training set including patient-specific data, to make an accurate prediction. Single-shot learning may utilize different neural network architectures to classify or recognize new instances with only one example. The approaches may include Matching Networks, Siamese Networks, and Memory-Augmented Neural Networks (MaNNs) Matching Networks may function by learning separate embedding functions for a support set and a query set. The model may classify the query by comparing its embedding to those in the support set through a nearest-neighbor search. Convolutional Neural Networks (CNNs) may be used to calculate these embeddings, allowing the model to apply gradient descent and attention mechanisms to enhance learning speed. Siamese Neural Networks may optimize a triplet loss function to compare input samples to a reference point. Two identical sub-networks may process the anchor, a positive sample related to the reference point, and a negative sample unrelated to the reference point. The network may maximize the distance between the anchor and the negative sample while minimizing the distance between the anchor and the positive sample. Memory-Augmented Neural Networks (MaNNs) may include a memory component consisting of a controller, read/write heads, and a memory module. The controller may write patterns, relationships, and context into the memory module while also reading from it to classify a query sample. By comparing the query's features to those stored in memory, MaNNs may enable efficient learning in tasks requiring long-term memory retention.

With continued reference to FIG. 1, at least a processor may be configured to transform a reference electrode 128 of the first electrode type and a query electrode 132 of the second electrode type such that a comparison may be made between a potential signal of the reference electrode 128 and the voltage of the query electrode 132. The reference electrode 128 provides a stable, baseline voltage, while the query electrode 132 captures variable potential signals from a specific area. These two electrodes may be of different types or have different characteristics, so the raw data they collect may not be directly comparable. The processor may be configured to adjust, normalize, or transform the data from both electrodes, ensuring that any differences in signal type, scale, or format are accounted for. This transformation allows the system to accurately compare the voltage measurements from the reference and query electrode 132, enabling the analysis of electrical activity in a specific region. Transformation may be referred to as conversion, normalization and/or normalizing. Normalizing plurality of potential signals 136 of the one or more non-identical electrodes may include instantiating a normalization machine-learning model, receiving a first type of electrode data having a first type of electrode characteristic, receiving a second type of electrode data having a second type of electrode characteristic, and converting, using transformation machine-learning model 160, the first type of electrode data having a first type of electrode characteristic into a first type of electrode data having a second type of electrode characteristic. The output of transformation machine-learning model 160 may directly be transferred to the next step and/or be displayed at a display device. As used herein, a "display device" refers to an electronic device designed to visually present information, images, or video to a user. Instantiation of transformation machine-learning model 160 may include generating transformation training data 164, training the transformation machine-learning model 160, and determining, using the transformation machine-learning model 160, scaled voltages or potentials of the one or more non-identical electrodes. In one or more embodiments, transformation training data 164 includes exemplary inputs such as, but without limitation, voltage pairs measured using the one ore more non-identical electrodes at a same location correlated with exemplary scaled voltages. Training of the model may take place at processor and/or remotely. Additionally, outputs of transformation machine-learning model may be iteratively reused as new transformation training data to update normalization machine-learning model. Updates to transformation machine-learning model may occur at processor and/or remotely. In a nonlimiting example, transformation machine learning model described herein may be consistent with any normalization machine-learning model disclosed in U.S. patent application Ser. No. 18/911,857, filed on Oct. 10, 2024, and entitled "APPARATUS AND METHOD FOR DETERMINING A NORMALIZED VOLTAGE ACROSS NON-IDENTICAL ELECTRODES" the entirety of which is incorporated herein by reference. In some embodiments, the electrode position signals may be determined using a model as disclosed in U.S. patent application Ser. No. 18/920,065, filed on Oct. 18, 2024, and entitled "SYSTEMS AND METHODS FOR ARTIFICIAL INTELLIGENCE ASSISTED MEDICAL DEVICE LOCALIZATION," the entirety of which is incorporated herein by reference.

With continued reference to FIG. 1, at least a processor 108 may be configured to receive at least a first signal 168 wherein the first signal includes a potential signal of the plurality of potential signal and the magnetic data. In an embodiment, receiving at least a first signal includes receiving a first potential signal 172 from the reference electrode 128, receiving a second potential signal 176 from the query electrodes 132, and normalizing the second potential signal 176 with respect to the first potential signal 172. In an embodiment, a potential signal may represent the voltage or electrical activity detected at a specific point, such as when electrodes in the at least a Catheter 116 is configured to measure the electrical impulses of the heart. The magnetic data may be configured to track the location and orientation of the plurality of electrodes or at least a catheter in the patient or saline tank. In an embodiment, the at least a processor 108 uses the plurality of potential signals and magnetic data to interpret the electrical activity and exact location where these signals are being captured. Normalizing the second potential signal 176 with respect to the first potential signal 172 may include adjusting the second potential signal 176 so that it can be compared to or combined with the first potential signal. In an embodiment, the first potential signal may serve as a reference point for normalization. The at least a processor 108 may then adjust the second signal in comparison to the first potential signal, to align the two sets of signals so the readings may be completed together. For example, the first potential signal may represent the baseline, while the second potential signal may be adjusted in relation to it. In another non-limiting embodiment, normalizing the second potential signal with respect to the first potential signal includes an electrode type transformation model 180. The electrode type transformation model 180 may be a machine-learning model trained using electrode type transformation training data configured to correlate potential signal readings from the first electrode type to potential signal readings from the second electrode type. The electrode type transformation model may be trained using historical inputs and outputs of previous iterations of the electrode type transformation model. The electrode type transformation model may incorporate user feedback regarding the accuracy of the generated outputs as training data into the electrode type transformation model. The electrode type transformation training data may use examples of potential signal readings from example electrode types correlated to potential readings from example types of second electrode types. The electrode type transformation model may be iteratively updated as new information regarding potential signal readings becomes available. In an embodiment, the electrode type transformation model is used to optimize the normalizing of the second potential signal with respect to the first potential signal includes an electrode type transformation model, at least by applying adjustments or calibrations specific to each type of electrode. Raw signals from different electrodes may be misaligned initially, which can result in accurate comparisons, the electrode type transformation model may adjust signals so that the differing signals can be aligned, regardless of the specific electrode types. The electrode type transformation model may enhance signal processing workflow by eliminating manual calibration or additional complex steps typically required to normalize the signals.

With continued reference to FIG. 1, the at least a processor 108 may be configured to generate, using the retrained mapping machine-learning model, as a function of the at least a first signal, a first position signal 184 for an electrode of the plurality of electrodes. Generating a first position signal 184 for an electrode of the plurality of electrodes includes using the retrained mapping machine-learning model 152 with the second training set to generate the first position signal for the query electrode 132. In an embodiment, the retrained mapping machine-learning will apply the at least a first signal as an input and output a first position signal for an electrode of the plurality of electrodes.

With continued reference to FIG. 1, the at least a processor 108 may be configured to validate the first position signal by generating a cross-electrode validation 188. As used herein, "cross-electrode validation" may refer to a process used to ensure the accuracy of the first position signal by comparing it with data from other nearby electrodes. In an embodiment, for cross-electrode validation 188, the plurality of electrodes can be positioned in close proximity of each other within a body tissue or saline tank. Each electrode of the plurality of electrodes may be configured to capture potential signals and position signals from each electrode. The cross-electrode validation 188 may perform correlation calculations between signals from different electrodes of the plurality of electrodes. In an embodiment, cross-electrode validation may be performed in real-time, to allow for immediate detection of inconsistencies. In an embodiment, if a signal from one electrode is found to be unreliable, the system can adjust in real-time by recalibrating the electrode's data or relying more heavily on surrounding electrodes data. The at least a processor 108 may be configured to transform potential signal readings across the plurality of electrodes using the cross-electrode model validation. In an embodiment, transforming potential signal readings using the cross-electrode model validation may include the correlation techniques employed by the cross-electrode model validation to ensure that the received signals detected align as expected, based on their relative positions and the known characteristics of the tissue being measured.

With continued reference to FIG. 1, in a non-limiting embodiment, a point-wise system may be used to evaluate trained models within system 100. In a non-limiting embodiment, the point-wise system may involve analyzing the accuracy of predicted positions or signals by evaluating the error between the true and predicted points in three-dimensional space (x, y, z coordinates). The analysis consists of two key metrics, Root Mean Square Error (RMSE) and a cumulative plot of Euclidean error with a focus on the top 90% of the data.

In an embodiment, a formula that may be used to calculate RMSE is:

$$RMSE = \sqrt{\left(\frac{1}{N}\sum_{i=1}^{n}\left((x_i - x'_i)^2 + (y_i - y'_i)^2 + (z_i - z'_i)^2\right)\right)}$$

Where $(x_i, y_i, z_i)$ are the true positions and $(x'_i, y'_i, z'_i)$ are the predicted positions for each point i, and n is the total number of points.

In an embodiment, a formula that may be used to calculate Euclidean Error is:

$$EuclideanError = \sqrt{((x_i-x'_i)^2 + (y_i-y'_i)^2 + (z_i-z'_i)^2)}$$

In non-limiting embodiments, at least a processor 108 may use mesh-based metrics to evaluate trained models within system 100. Mesh-based metrics may include mean square metric configured to calculate the mean square error between two sets of vertices by comparing at least the geometry of the position signals. Specifically, for each triangle on the query node, the function identifies its closest corresponding points on the reference node and computes the error between these points. The MSE is then derived by averaging the squared differences between the positions of the corresponding points across the two objects. This metric provides a measure of how well the two objects align, with a lower MSE indicating a closer match. In another embodiment, at least a processor 108 may use mean error metric to calculate individual distances between corresponding points on the source and query nodes. In an embodiment, Mean Error Metric evaluates individual distances that are also squared but immediately square-rooted after, making the error more proportional to the actual distances. The final mean error is the cumulative error divided by the total area, without the additional squaring and root operations. This provides a more direct representation of the average error across the surface, without disproportionately amplifying larger deviations. In another non-limiting embodiment, at least a processor 108 may use Hausdorff distance as a metric that quantifies the difference between two subsets of a metric space, essentially measuring how far apart two shapes or objects are from each other. This makes it especially useful in applications like shape matching, where it helps determine how well two shapes align by highlighting the maximum deviation between their boundaries. The Hausdorff distance is often used to evaluate the similarity between geometric structures in computer vision, pattern recognition, and 3D modeling, such as for cardiac mapping.

Referring now to FIG. 2A, a diagram illustrating an exemplary embodiment of a catheter with electrodes in a grid orientation. A grid of electrodes 204a is shown. In an embodiment grid of electrodes 204a may include a plurality of electrodes. Further these electrodes may be flexible electrodes. In one or more embodiments, an individual electrode within grid of electrodes 204a may be 1 mm in length. In such an embodiment, each individual electrode within the grid of electrodes 204a may be spaced 3 mm from each other individual electrode of the grid of electrodes 204a. catheter 200a may additionally include one or more shaft electrodes 208a. Shaft electrodes 208a may be rigid electrodes and located on the shaft of catheter 200a, proximal to grid of electrodes 204a. Furthermore, catheter 200a may include a magnetic sensor 212a. Magnetic sensor 212a may be located on the shaft of catheter 200a, proximal to grid of electrodes 204a and situated between the one or more shaft electrodes 208a. Catheter 200a is an exemplary embodiment of a catheter that may be integrated with system 100.

Referring now to FIG. 2B, a diagram illustrating an exemplary embodiment of a catheter with electrodes in a straight-line orientation. Catheter 200b is yet another exemplary embodiment of a catheter that may be integrated with system 100. Here, catheter 200b includes a contact force sensor 204b, an electrode magnetic sensor 208b, and a braided structure 212b. Contact force sensor 204b may be located behind the distal tip of catheter 200b. Proximal to contact force sensor 204b is where electrode magnetic sensor 208b may be located and is illustrated in FIG. 2B. Further, catheter 200b may integrate a unique braided structure 212b. Braided structure 212b may increase shaft pliability compared to proximal shaft. Additionally, catheter 200b may include 2-2-2 ring spacing for evenly spaced bipole pairs. Lastly, the interior of catheter 200b may include three fiber optic sensing cables. This embodiment, and others not specifically disclosed within may be seamlessly integrated into system 100.

Figure 3:
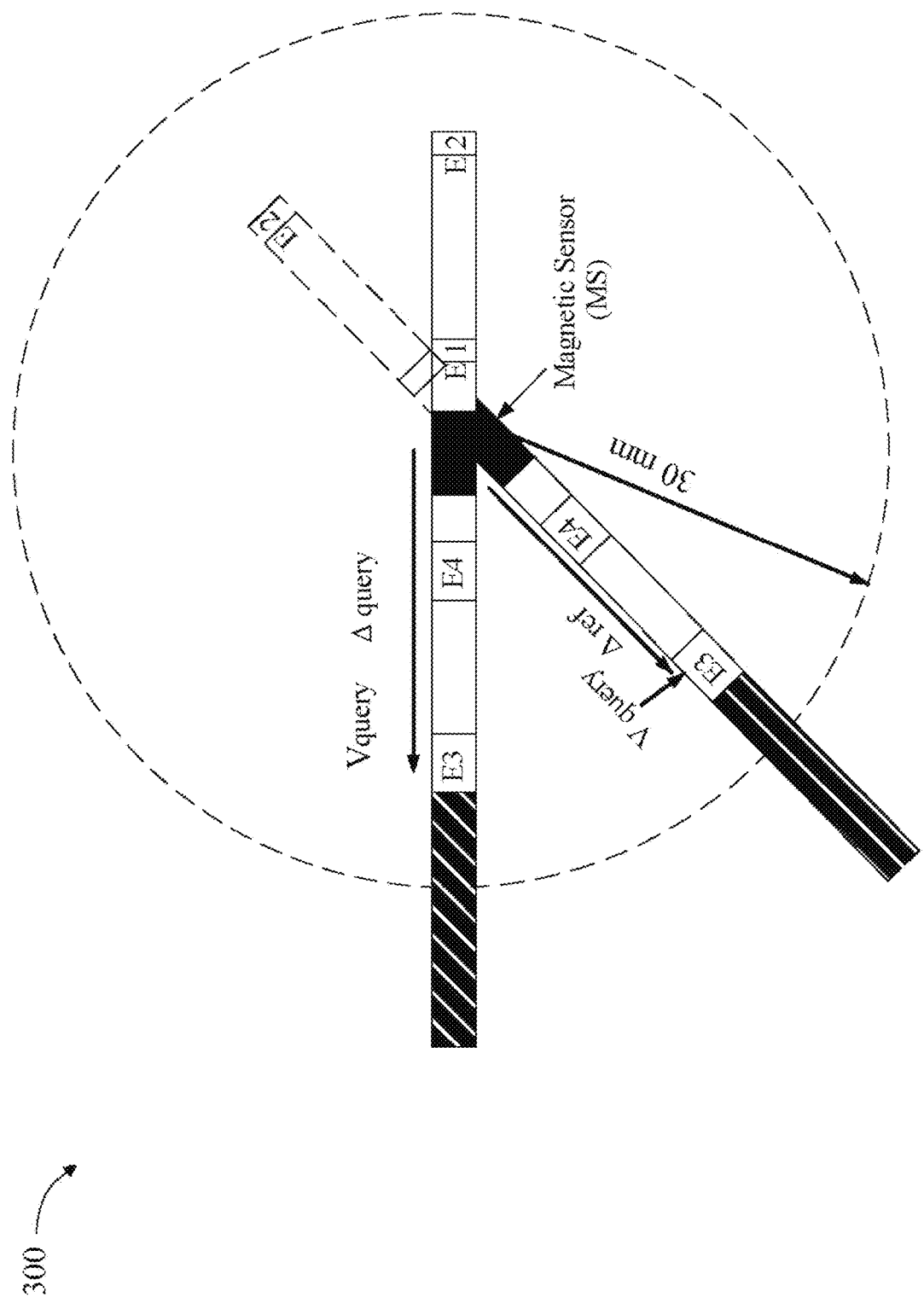
FIG. 3 is a diagram of an exemplary embodiment of the at least one or more sensors of a medical device using one or more rigid electrodes as a reference electrode.

Referring now to FIG. 3 a diagram of a particular implementation of a system for AI-assisted medical device localization 300, specifically illustrating an exemplary embodiment of the at least one or more sensors of a medical device using one or more rigid electrodes as a reference electrode 128. Illustrated in FIG. 3 are two types of electrodes. Electrodes E1 and E2 on the flexible portion are smaller in size compared to E3 and E4. Further, E1 and E2 are located on the flexible portion of the catheter, meaning there is an ability to bend the catheter in this area. Electrodes E3 and E4 on the rigid portion are larger than E1 and E2 and there is no ability in which to bend the catheter with respect to the lined portion of the stem. A magnetic sensor is embedded in the rigid portion itself. Thus, there are two sets of non-identical electrodes: first set {E1, E2} and a second set {E3, E4}. The electrodes may vary from each other due to their material type, size, shape, and/or electrical characteristics. The voltage read by the electrodes of different types will be different at the exact same location x, y, z in the field. Therefore, to formulate a generic mapping formulation the voltages must be scaled or otherwise normalized.

Figure 4:
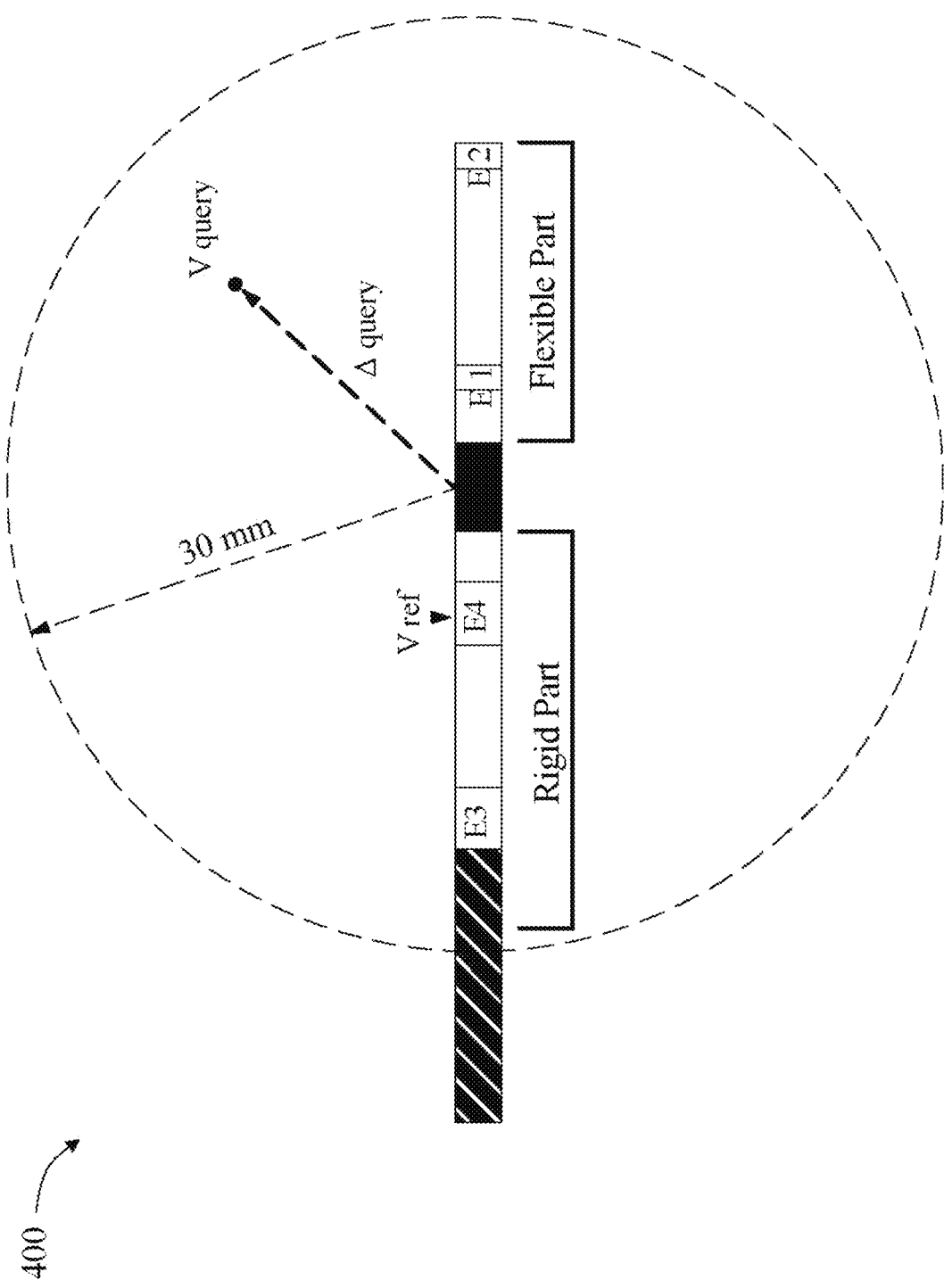
FIG. 4 is a diagram of an exemplary embodiment of the at least one or more sensors of a medical device using one or more non-rigid electrodes as a reference electrode.

Referring now to FIG. 4, a diagram of a particular implementation of a system for AI-assisted medical device localization 400, specifically illustrating an exemplary embodiment of the at least one or more sensors of a medical device utilizing non-rigid electrodes. Here, rather than rigid electrodes being the reference electrode 128, flexible electrodes are able to serve as reference electrode 128 after the training of the localization model.

Figure 5:
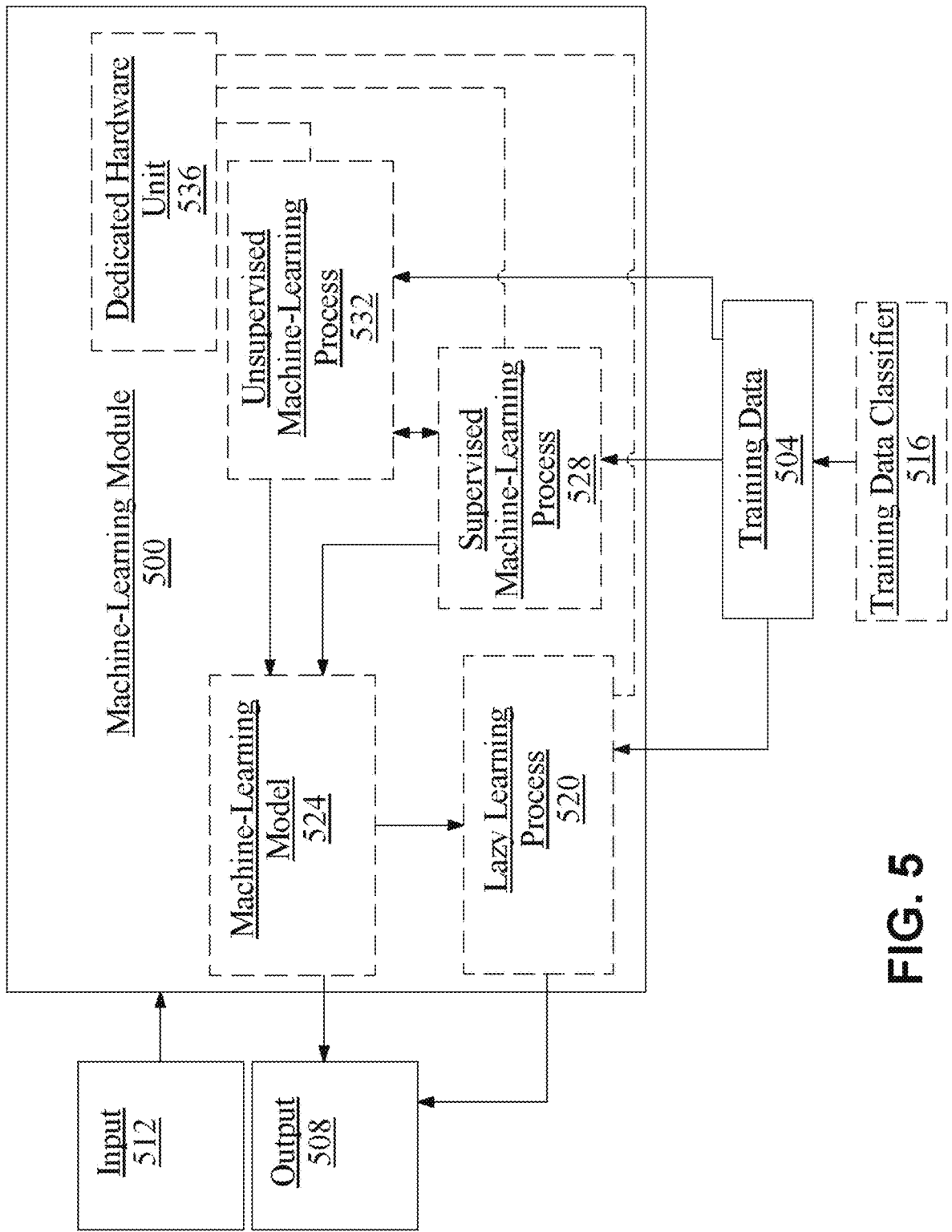
FIG. 5 is a block diagram of an exemplary machine-learning process.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine-learning processes. A "machine-learning process," as used in this disclosure, is a process that automatedly uses training data 504 to generate an algorithm instantiated in hardware or software logic, data structures, and/or functions that will be performed by a computing device/module to produce outputs 508 given data provided as inputs 512; this is in contrast to a non-machine-learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example magnetic sensor location data, reference electrode 128 voltage and position data, and query electrode 132 voltage data correlated with query electrode 132 position data.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a data structure representing and/or using a mathematical model, neural net, or program generated by a machine-learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to scale or normalize electrical characteristics across non-identical electrode types.

Still referring to FIG. 5, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)+P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 5, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 5, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 5, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 5, computer, processor, and/or module may be configured to preprocess training data. "Preprocessing" training data, as used in this disclosure, is transforming training data from raw form to a format that can be used for training a machine-learning model. Preprocessing may include sanitizing, feature selection, feature scaling, data augmentation and the like.

Still referring to FIG. 5, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 5, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 5, computing device, processor, and/or module may be configured to precondition one or more training examples. For instance, and without limitation, where a machine-learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine-learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine-learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 5, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Antialiasing and/or anti-imaging filters, and/or low-pass filters, may be used to clean up side-effects of compression.

Further referring to FIG. 5, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 5, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 5, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include any inputs as described above as inputs, any outputs as described throughout this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

With further reference to FIG. 5, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 5, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 5, machine-learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 532 may not require a response variable; unsupervised processes 532 may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 5, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 5, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 5, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 5, one or more processes or algorithms described above may be performed by at least a dedicated hardware unit 536. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 536 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 536 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 536 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 6:
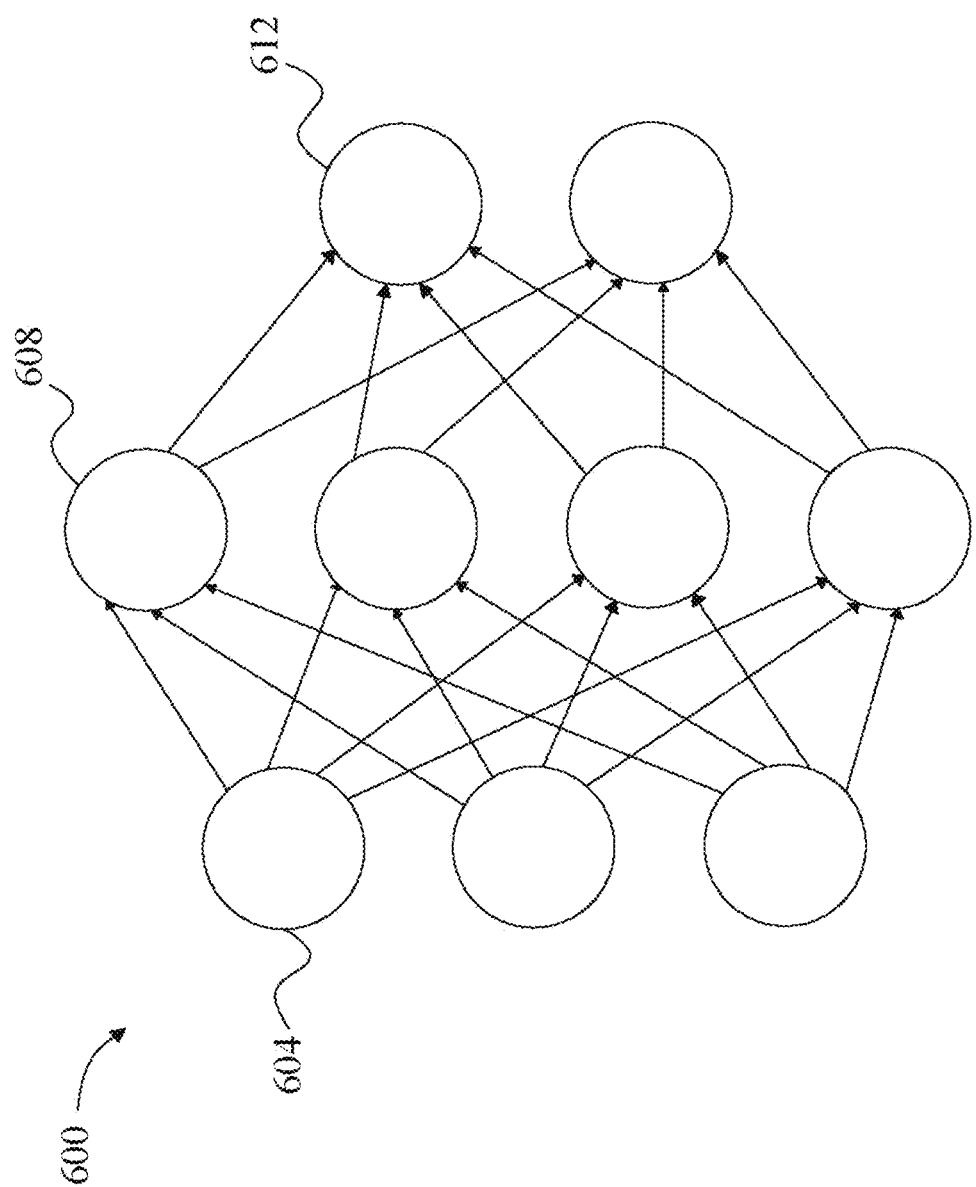
FIG. 6 is a diagram of an exemplary embodiment of a neural network.

Referring now to FIG. 6, an exemplary embodiment of neural network 600 is illustrated. A neural network 600 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 604, one or more intermediate layers 608, and an output layer of nodes 612. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 7:
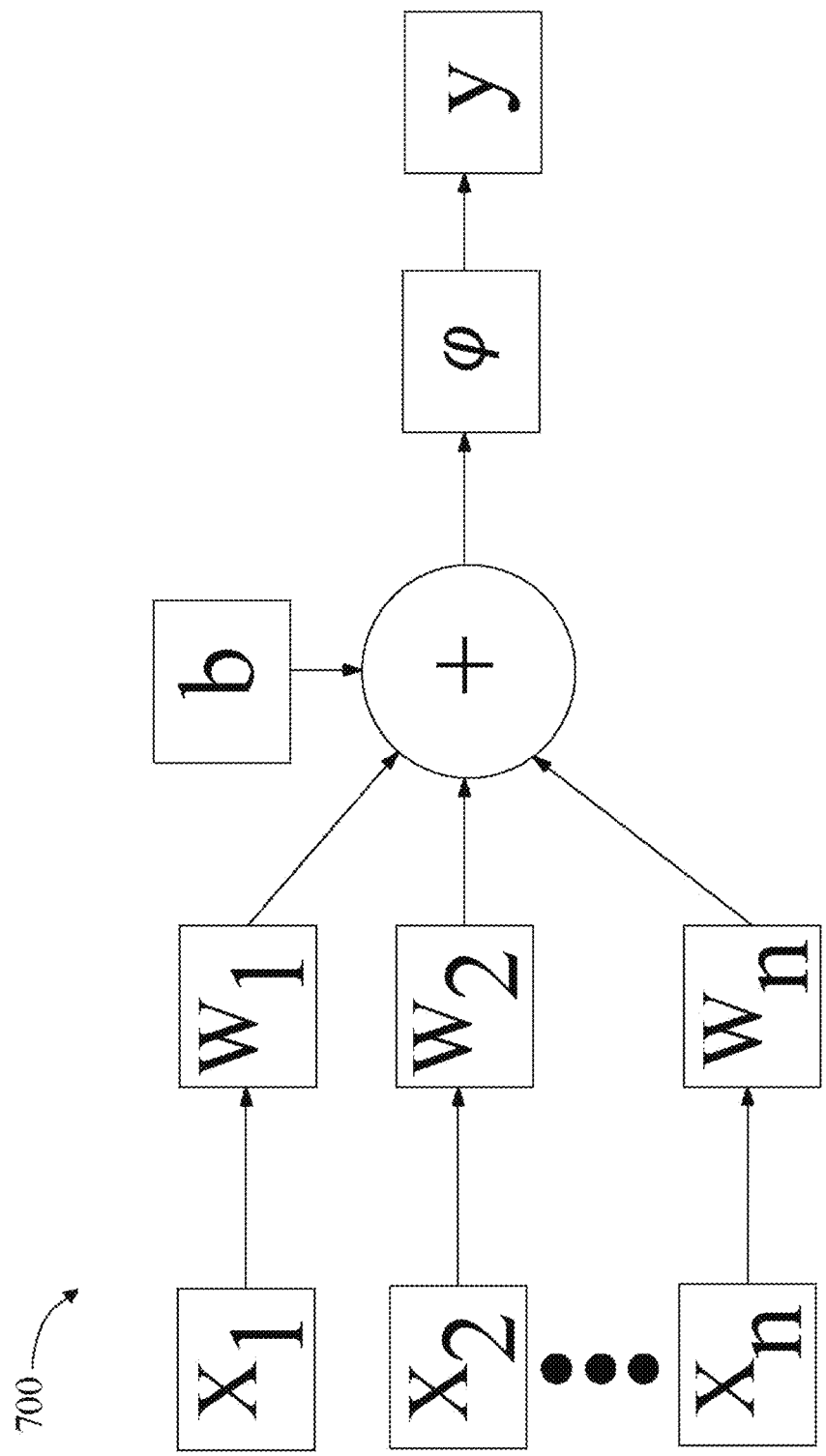
FIG. 7 is a diagram of an exemplary embodiment of a node of a neural network.

Referring now to FIG. 7, an exemplary embodiment of a node 700 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 8:
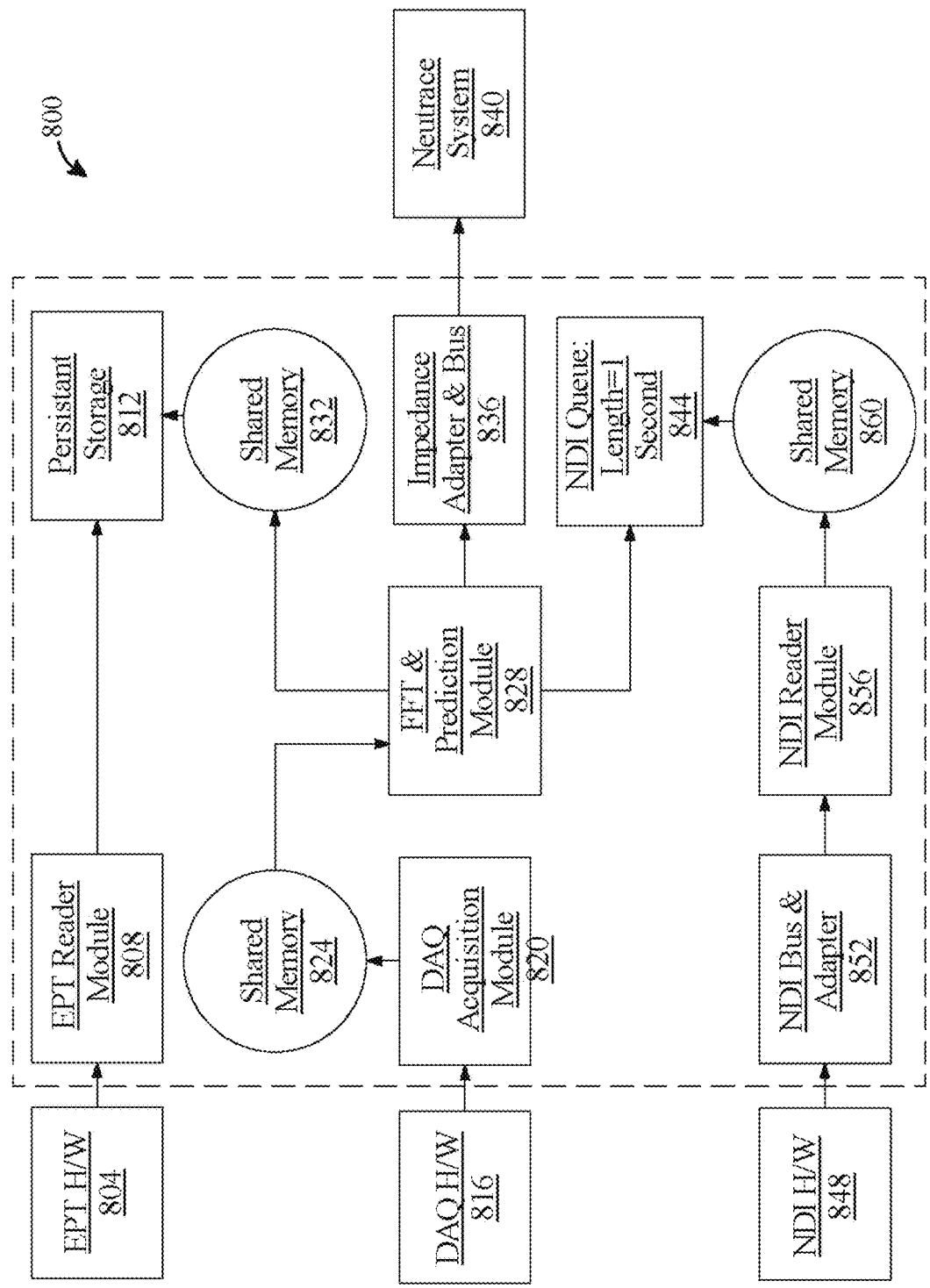
FIG. 8 is a flow diagram of an exemplary embodiment of a software flow for various modules.

Now referring to FIG. 8, illustrated is an exemplary software flow diagram of system 800 for various modules. EPT H/W 804 is an electrophysiology tracer, which is configured to measure and record intracardiac and ECG voltage measurements. EPT H/W 804 may have dedicated channels for surface ECG patches, and catheter signals, which may come through a change control board (CCB) box after splitting them. EPT H/W 804 may work at a sampling rate of 1 kHz and thus suitable for signals within the 0-500 Hz range. The rate of the intracardiac signal being measured by EPT H/W 804 may be 1000 samples per second across all channels (i.e., surface ECG and EMG signals). The internal circuitry of EPT H/W 804 may provide provision for filtering and amplifications per channel. Within system 800 EPT H/W may input data as discussed above, into EPT Reader Module 808. EPT Reader Module 808 may include a model architecture as described throughout this disclosure, for example and without limitation, such as model 900 discussed below. EPT Reader Module 808 may output logs, or otherwise write logs to disk and send said logs to persistent storage 812. As used here, and throughout this disclosure, "persistent storage" is a data storage device that can retain data even when the device is powered off or disconnected from a system.

Still referring to FIG. 8, DAQ H/W 816 is a data acquisition system. Signals from one or more catheter pins may be split and fed to EPT H/W 804 as well as to DAQ H/W 816. An exemplary DAQ H/W 816 is a system built by National Instruments (NI). DAQ H/W 816 may connect to the processing computer via a LAN interface. DAQ H/W may input collected data into DAQ acquisition module 816. Within DAQ acquisition module 816 there may be any one and/or combination of three types of modules: (1) patch voltage generation module with six channels and +/−10 V range; (2) patch voltage measurement module with +/−10 V, 12 bit resolution, and 8 channels; and (3) catheter voltage measurement module with a max range of +/−1V with 16-bit resolution, giving a sensitivity of 15 microvolts. The acquisition rate for all the measurement modules is 30 KHz, thus providing a time resolution of 33 microseconds. From DAQ acquisition module 816 outputs may be sent to shared memory 824. For example, and without limitation buffer data may be written ever 100 ms. From shared memory 824 buffer data may be read by FFT and prediction module 828. FFT stands for Fast Fourier Transform, which is a mathematical algorithm that converts time-domain data into a frequency-domain representation. From FFT and prediction module 828 three potential paths exist as discussed below.

As further disclosure regarding FFT and prediction module 828, 100-millisecond window of signal measurements at every 100 ms are acquired. Thus, the read frequency provides 10 windows of 100 ms per second. Windowing of the signal allows for continuous signal measurement of a varying signal and can be estimated over a sufficient window to counter any noise-related erroneous values. To estimate the voltage emerging due to the subjected electrical field, FFT is used as a way to measure the voltage response of every electrode within an acquired window. One window of the data acquired via DAQ H/W 816 may present as such: [tDAQ, V buffer window]. Where, $t_{DAQ}$ is mid time of the acquisition window; $V_{buffer\ window}$ is an $R^{n \times z}$ matrix where n is the number of electrodes being tracked DAQ, and z is 2000 for 30 KHz sampling rate and 100 ms window. In one or more embodiments, a conditioning step may occur for each electrode. In such an embodiment, the signal conditioning step may have a mean subtraction, zero padding, and a Hanning window before FFT. After FFT a peak detection may occur, wherein the amplitudes of the normalized voltage are taken at the patch frequencies. For the $i^{th}$ electrode, we get $V_i^{f1}, V_i^{f2}, \ldots, V_i^{fj}, \ldots V_i^{fm}$ where f1, ..., fm are m excitation frequencies. The DAQ data after signal conditioning may present as such: $[t_{DAQ}, V_1^{f1}, V_1^{f2}, \ldots, V_1^{fj}, \ldots V_1^{fm}, V_2^{f1}, V_2^{f2}, \ldots, V_2^{fj}, \ldots, V_2^{fm}, \ldots, V_i^{f1}, V_i^{f2}, \ldots, V_i^{fj}, \ldots V_i^{fm}, \ldots, V_n^{f1}, V_n^{f2}, \ldots, V_n^{fj}, \ldots, V_n^{fm}]$ Continuing to reference FIG. 8, from FFT and prediction module 828 buffer data and FFT data along with matched timestamps may be written on shared memory 832. Further shared memory 832 may write buffer data and FFT data to HDF5 on storage at persistent storage 812. Alternatively from FFT and prediction module 828 predictions may be sent via network to impedance adapter and BUS 836, wherein impedance adapter and BUS 836 may communicate said predictions via Rabbit MQ to Neutrace system 840. Additionally, and alternatively, from FFT and prediction module 828 buffer data may be read for the closest NDI record by timestamp matching at NDI queue: length=1 second 844.

Further referencing FIG. 8, Neutrace system 840 may be configured to run on a centralized rendering system, wherein all data streams are sent to said centralized rendering system. Neutrace system 840 is an interface where a user, such as a surgeon, may see the map involved in real-time along with the catheter electrodes being rendered to facilitate navigation. Apart form the geometry building, Neutrace system 840 may also be responsible for the point acquisition gating based on a user-defined template rhythm on the ECG and/or EGM signal.

In further reference to FIG. 8, NDI H/W 848 is a software program configured to facilitate magnetic field generation. NDI H/W 848 may operate in coordination with NDI field generator hardware, a software driver, and am adaptor code running on a computer system. NDI H/W 848 may employ a sophisticated method creating a cylindrical magnetic field, useful for high-precision tracking in medical procedures. NDI H/W 848 may utilize an electromagnetic transmitter equipped with multiple carefully arranged coils. Said coils may generate a magnetic field by passing an electrical current through them, producing a stable, predictable field within a cylindrical volume centered around the transmitter. The cylindrical shape of this field is designed to ensure consistent tracking accuracy within the operational area. Sensors may be embedded in medical instruments to detect variations in the magnetic field's strength and direction. NDI H/W 848 may process these variations to calculate the precise position and orientation of the sensors in real-time.

The cylindrical magnetic field is especially suited for procedures where maintaining precise control over instrument placement is crucial. For example, and without limitation, such as in catheter navigation and other minimally invasive interventions. NDI H/W 848 may possess measurement accuracy within a few millimeters. Positional accuracy of magnetic tracking systems, such as NDI H/W 848 may range from +/−1 mm to +/−2 mm. This means that the tracked position of the sensor is within this error range from its true position. The angular accuracy, which measures the precision of orientation tracking may fall within +/−1 degree to +/−2 degrees. In one or more embodiments, NDI H/W 848 may be configured to track one or more magnetic sensors and/or catheters simultaneously. NDI H/W 848 may be configured to track eight sensors and/or catheters using two signal interface units (SIU) and one signal control unit (SCU). The throughput of NDI H/W 848 is 33 samples per second, assuming a velocity range of 0-8 cm per second of the catheter and/or sensor tip. In an embodiment wherein the velocity is higher, NDI H/W 848 may provide a catheter missing warning/A typical sample of the magnetic data may be presented as such: $[t_m, MS_x^1, MS_y^1, MS_z^1, Q_0^1, Q_1^1, Q_2^1, Q_3^1, \ldots, MS_x^k, MS_y^k, MS_z^k, Q_0^k, Q_1^k, Q_2^k, Q_3^k, \ldots, MS_x^p, MS_y^p, MS_z^p, Q_0^p, Q_1^p, Q_2^p, Q_3^p]$. Wherein $t_m$ is the time of the reading and/or acquisition; $MS_x^k$ is magnetic sensor x location of the catheter (mm) for the k1 sensor and/or catheter; $MS_y^k$ is magnetic sensor y location of the catheter (mm) for the k1 sensor and/or catheter; $MS_z^k$ is magnetic sensor z location of the catheter (mm) for the k1 sensor and/or catheter; $Q_0^k, Q_1^k, Q_2^k, Q_3^k$, are quaternion coefficient providing orientation for the $k^{th}$ sensor and/or catheter; and p is the total number of catheters and/or sensors.

Continuing to reference FIG. 8, NDI H/W 848 may input data as discussed above into NDI BUS and adapter 852. From NDI BUS and adapter 852 data may be read every 100 ms via a transmission control protocol (TCP) at NDI reader module 856. Further, from NDI reader module 856 parsed NDI records may be written at shared memory 860. Which may further store recent one second NDI records at NDI queue: length=1 second 844.

Figure 9:
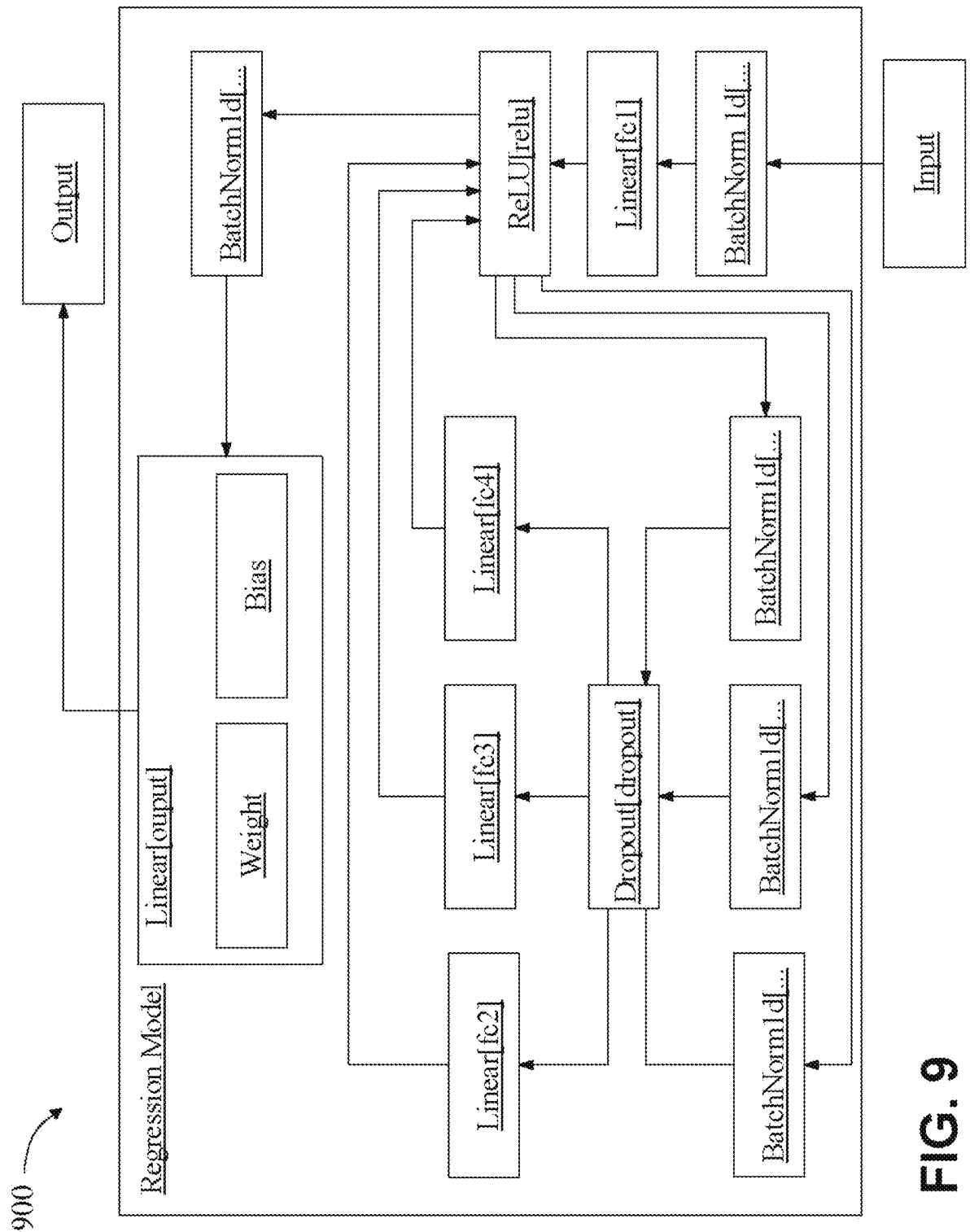
FIG. 9 illustrates an exemplary model architecture.

Now referring to FIG. 9, illustrated is an exemplary embodiment of model architecture 900. Model architecture 900 is a regression model including 3,867 total number of parameters. Exemplary inputs may be any input as described throughout this disclosure. Further, exemplary outputs may be any output as described throughout this disclosure.

Figure 10:
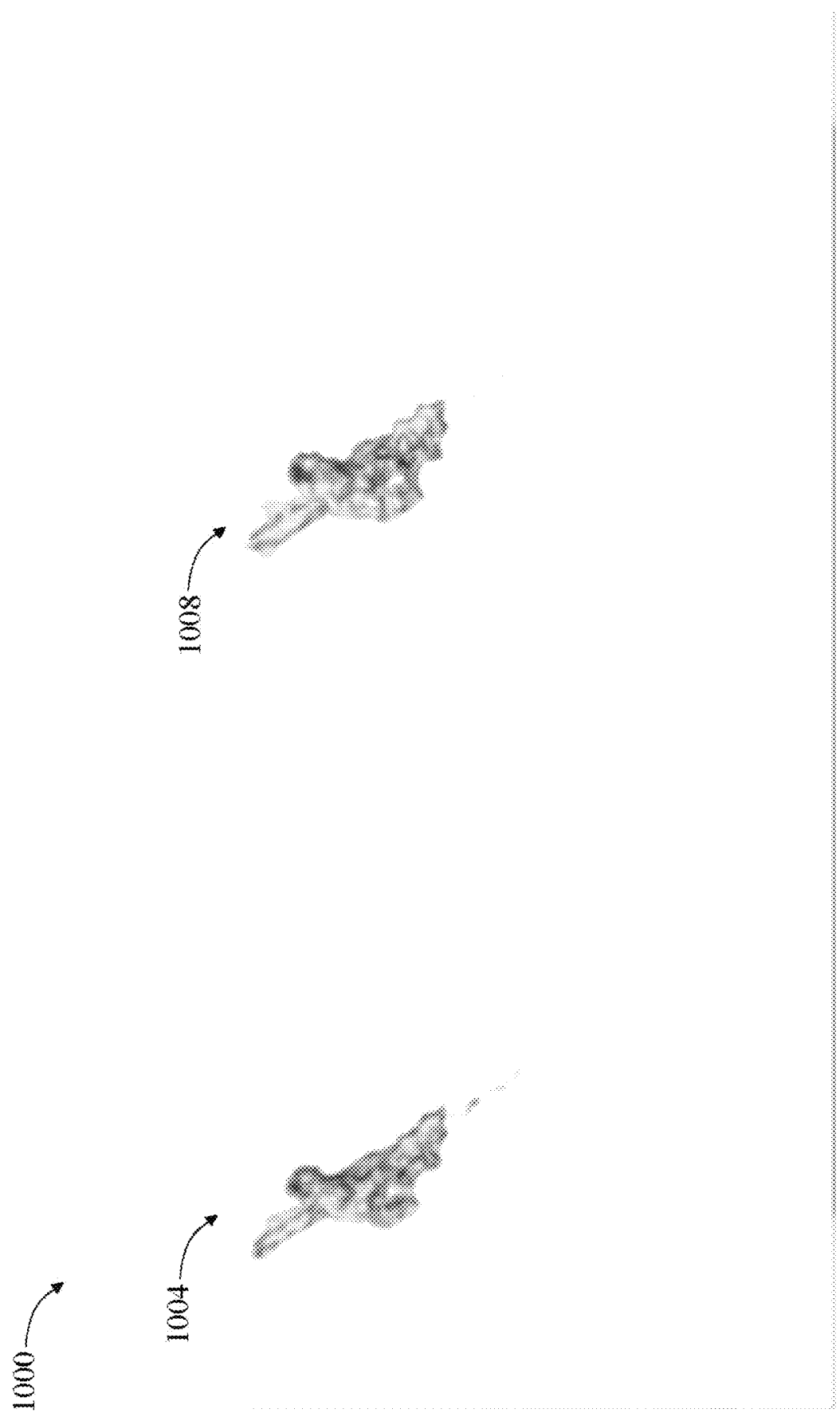
FIG. 10 illustrates an exemplary mesh comparison.

Now referring to FIG. 10, illustrated is an exemplary mesh comparison 1000. Exemplary mesh comparison 1000 highlights predicted mesh 10004 and actual mesh 10008. As used herein, "mesh" refers to a three-dimensional geometric model of the heart or a specific area of the heart. In an embodiment, actual mesh 10008 may be generated using cardiac mapping, an echocardiogram, intracardiac echocardiogram, magnetic resonance imaging, and the like. Predicted mesh 1004 may be generated using any of the methods described herein. Exemplary mesh comparisons may be calculated using any format described throughout this disclosure.

Now referring to FIG. 11A-D, illustrated is an embodiment of collected data for an animal study protocol. The protocol for the animal study is listed below:

TABLE 1

Animal Study Protocol

| Run | Chamber | Patch Placement | Field connectivity | Catheter |
|---|---|---|---|---|
| 1 | RA | Position A1 | Orthogonal | Tacticath |
| 2 | RA | Position A1 | 5 Active Patches | Tacticath |
| 3 | RA | Position B1 | 5 Active Patches | Tacticath |
| 4 | RA | Position B1 | Orthogonal | Tacticath |
| 5 | RA | Position B1 | 5 Active Patches | HD Grid |

Referring to Table 1: Animal Study protocol, Patch Placement' denotes a set of patches. Perturbing the patch on the animal body gives a new position set. Table 1: Animal Study Protocol shows an analysis of the collected data during the above procedure with various aspects. The exact location of the rigid electrodes is computed based on the MS and the rigid inter-electrode distances. For the flexible electrodes of the HDGrid, the exact location may be unknown. A frame of data means a set such that it has all voltage values across excitation frequencies and all electrodes along with their computed magnetic location at a given time instance. A table indicating the number of points recorded is listed below:

TABLE 2

Number of Points Recorded

| | | | | Number of points | |
|---|---|---|---|---|---|
| Run | Patch Placement | Field connectivity | Catheter | Total | Per electrode |
| 1 | A1 | ORT | TAC | 52004 | 13001 |
| 2 | A1 | 5 AP | TAC | 46836 | 11709 |
| 3 | B1 | ORT | TAC | 60144 | 15036 |
| 4 | B1 | 5 AP | TAC | 50416 | 12604 |
| 5 | B1 | 5 AP | HD Grid | 125100 | 6950 |
| 6 | B1 | 5 AP | HD Grid | 163962 | 9109 |
| | | | Total frame count | | 59300 |
| | | | Total imp-loc data pair | | 223300 |

Figure 11A:
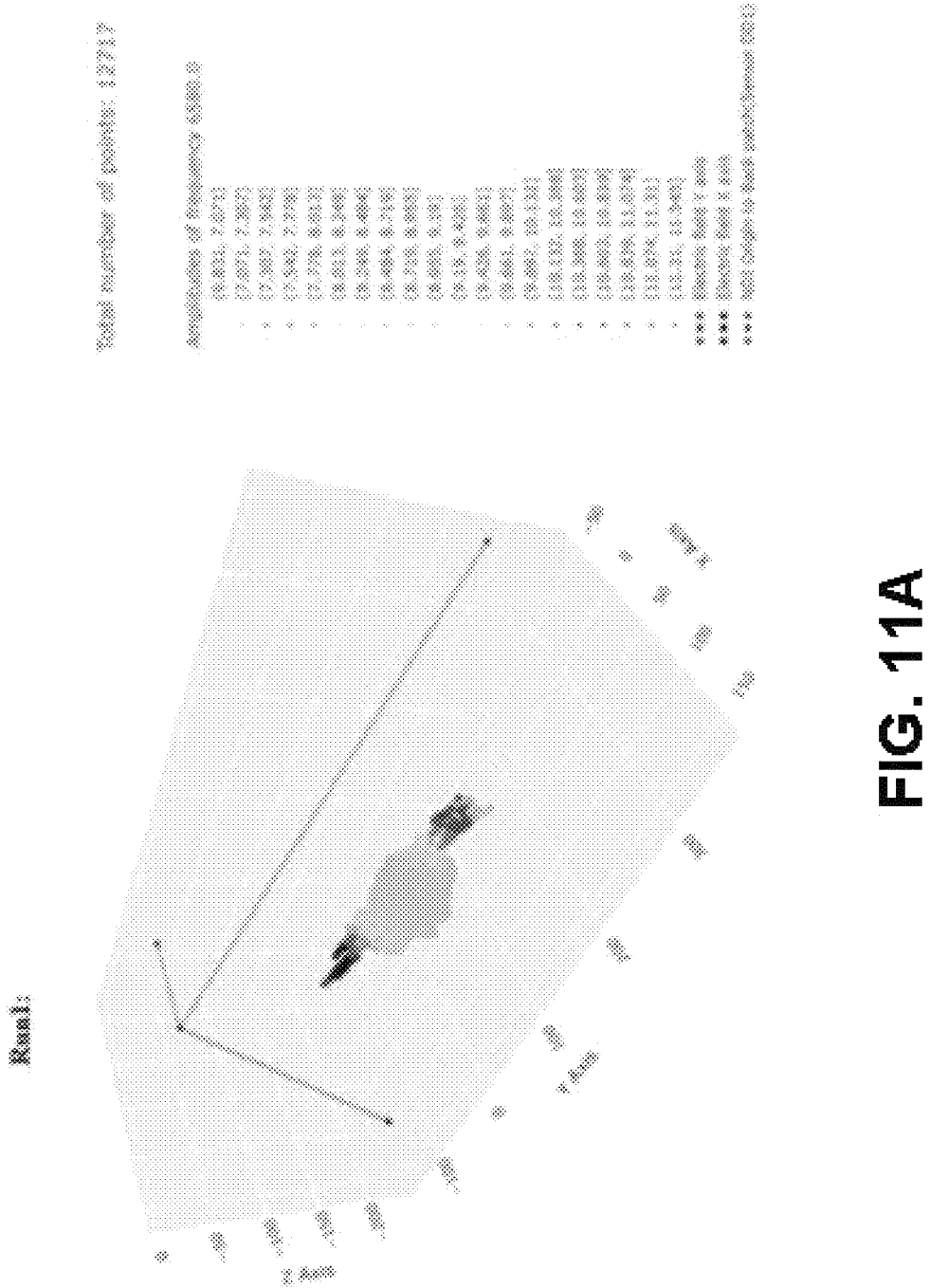
FIGS. 11A-D illustrate embodiments of collected data for an animal study protocol.

Referring now to FIG. 11A, illustrated is an embodiment of the collected data for Run 1. The plot depicted in FIG. 11A is of the FFT amplitudes of the frequency component 6580 HZ and electrode 2 from Tacticath. The units for the plot are in millivolts. The legend shows a binning of the voltages with their corresponding colors. Run 1 may be orthogonal using a single electrode.

Figure 11B:
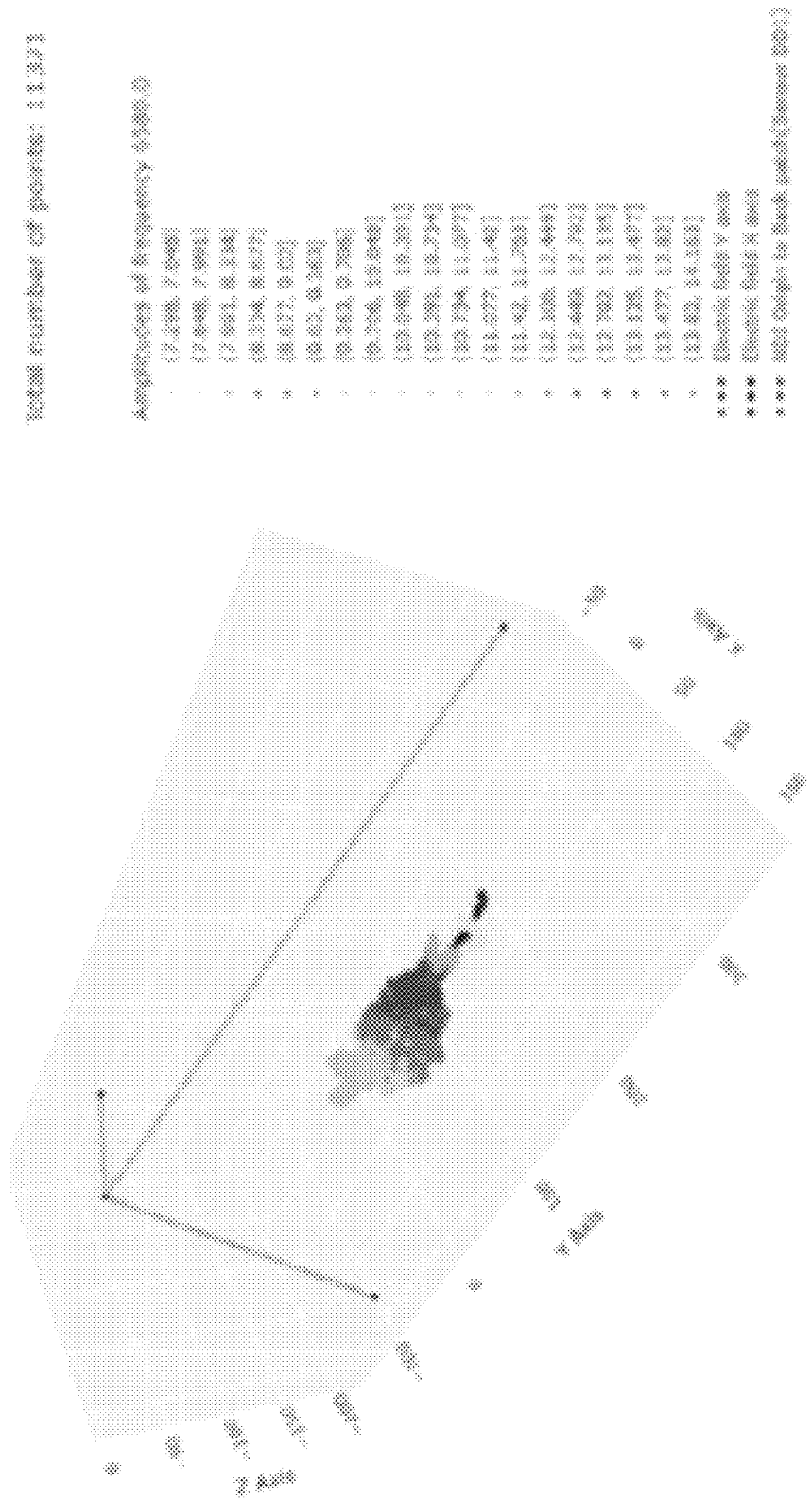

Referring now to FIG. 11B, illustrated is an embodiment of the collected data for Run 2. The plot depicted in FIG. 11B is of the FFT amplitudes of the frequency component 6580 Hz and electrode 2 from Tacticath. The units for the plot are in millivolts. The legend shows a binning of the voltages with their corresponding colors. Run 2 may use a 5 active patch configuration.

Figure 11C:
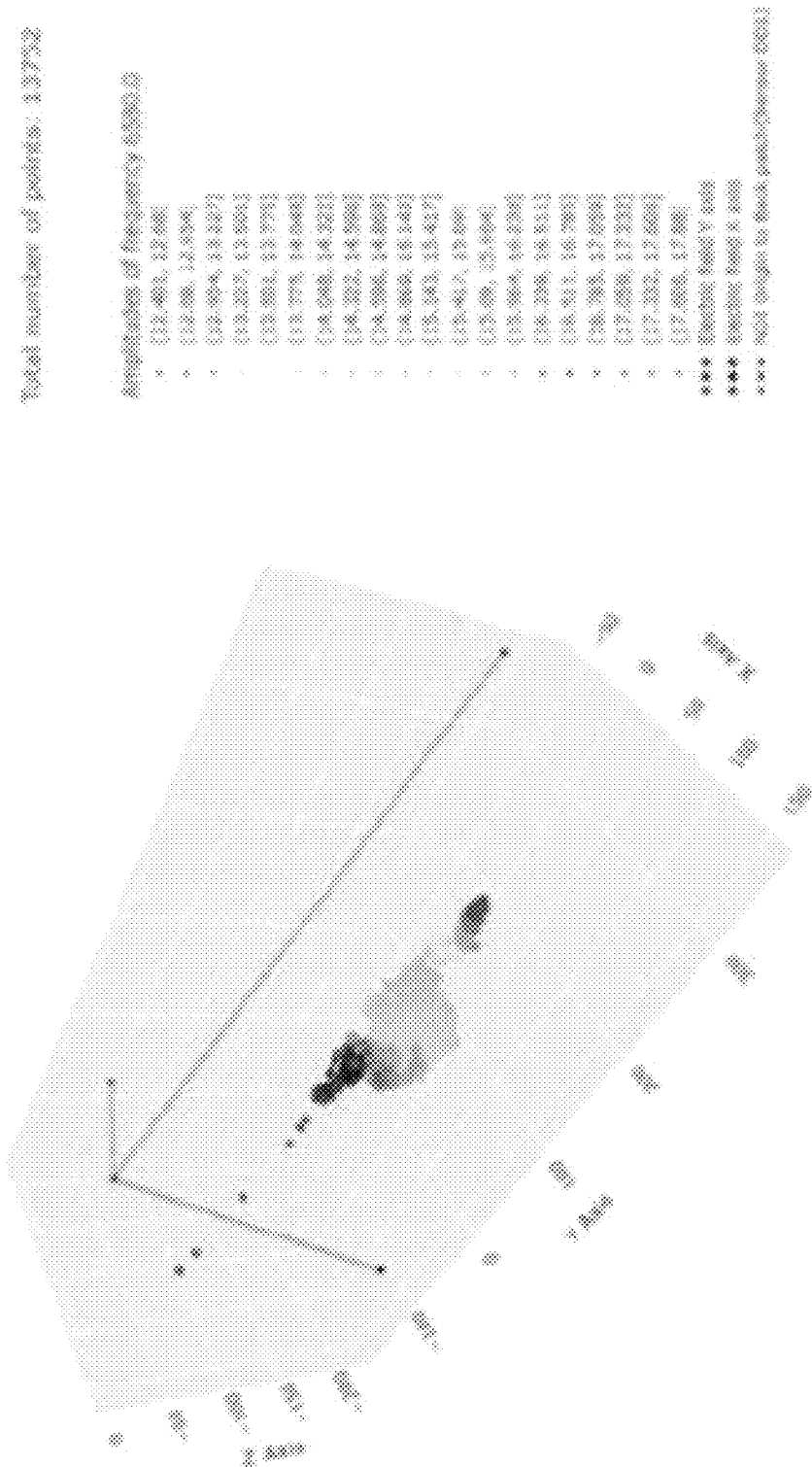

Referring now to FIG. 11C, illustrated is an embodiment for the collected data for Run 3. The plot depicted in FIG. 11C is of the FFT amplitudes of the frequency component 6580 Hz and electrode 2 from Tacticath. The units for the plot are in millivolts. The legend shows a binning of the voltages with their corresponding colors. Run 3 may use a single electrode.

Figure 11D:
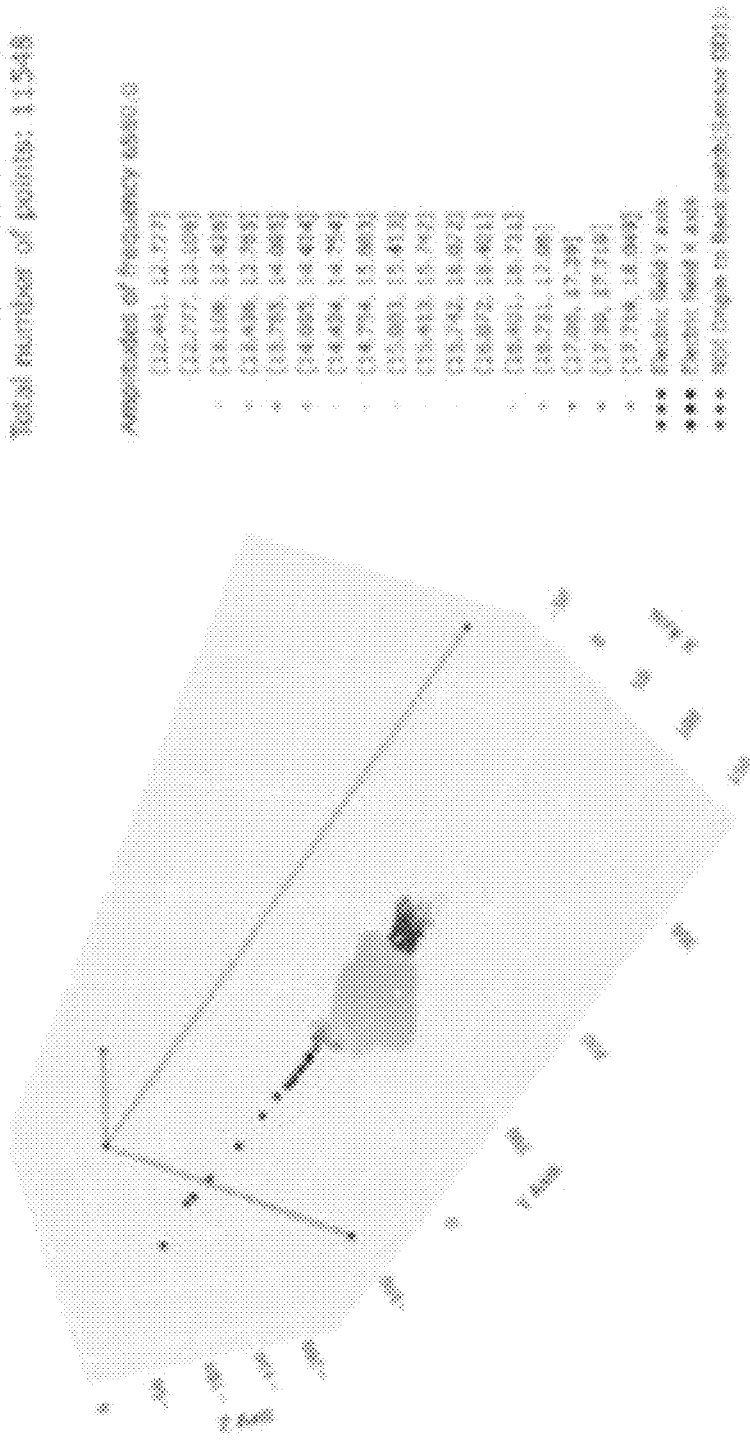

Referring now to FIG. 11D, illustrated is an embodiment for the collected data for Run 4. The plot depicted in FIG. 11D is of the FFT amplitudes of the frequency component 6580 Hz and electrode 2 from Tacticath. The units for the plot are in millivolts. The legend shows a binning of the voltages with their corresponding colors.

Figure 12A:
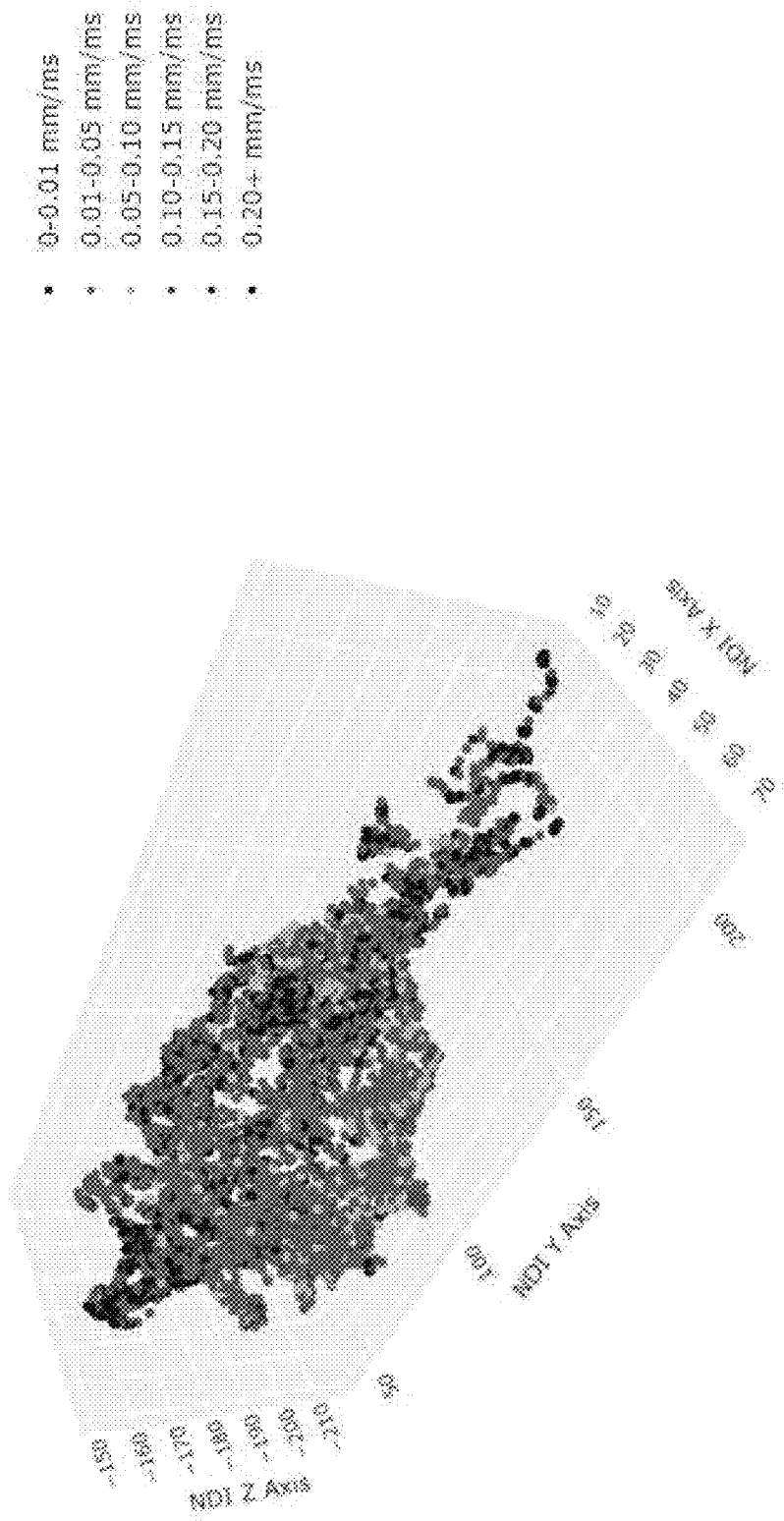
FIGS. 12A-B illustrate embodiments of a velocity plot.
Figure 12B:
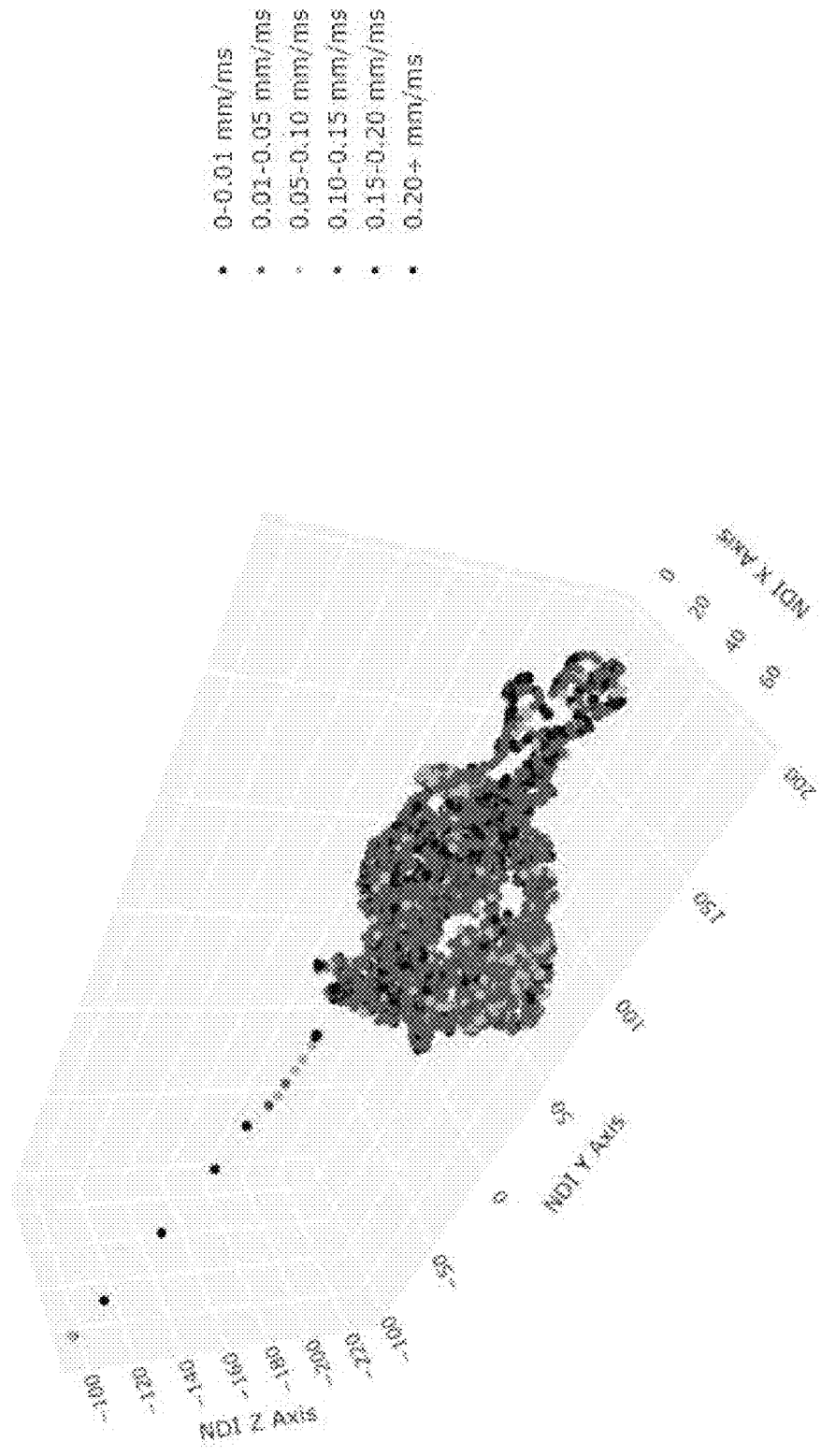

Referring now to FIG. 12A-B, illustrated is an embodiment of a velocity plot. The velocity plot is of the tip velocity of Tacticath. The legend shows a binning of the velocity with their corresponding color. Referring to FIG. 12A, illustrated is an embodiment of a velocity plot for run 2. Referring to FIG. 12B, illustrated is an embodiment of a velocity plot for run 4.

Figure 13A:
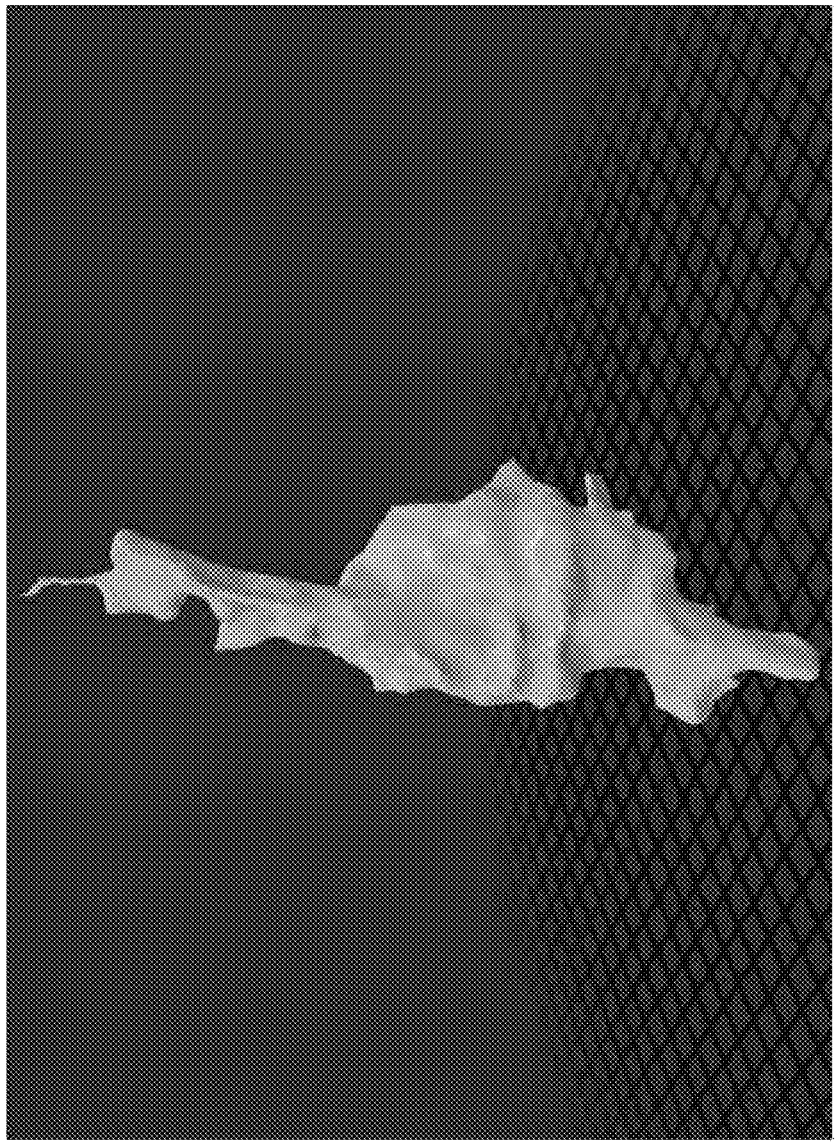
FIGS. 13A-B illustrate embodiments of a geometry bult by the magnetic locations of acquired points.
Figure 13B:
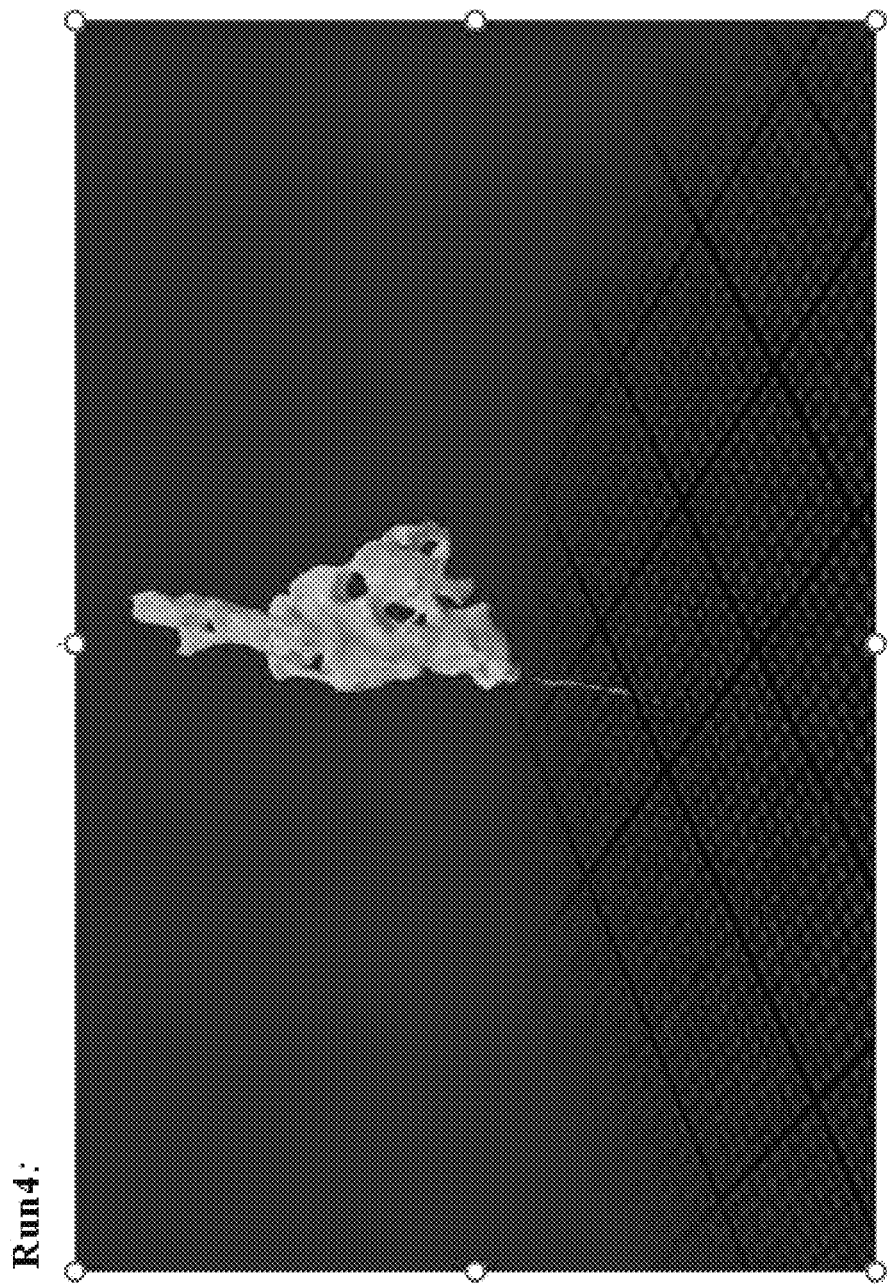

Referring now to FIG. 13A-B, illustrated is an embodiment of a geometry bult by the magnetic locations of acquired points. Referring to FIG. 13A, illustrated is an embodiment of the geometry built by the magnetic location of the Run2 acquired points. Referring to FIG. 13B, illustrated is an embodiment of the geometry built by the magnetic location of the Run4 acquired points.

Figure 14A:
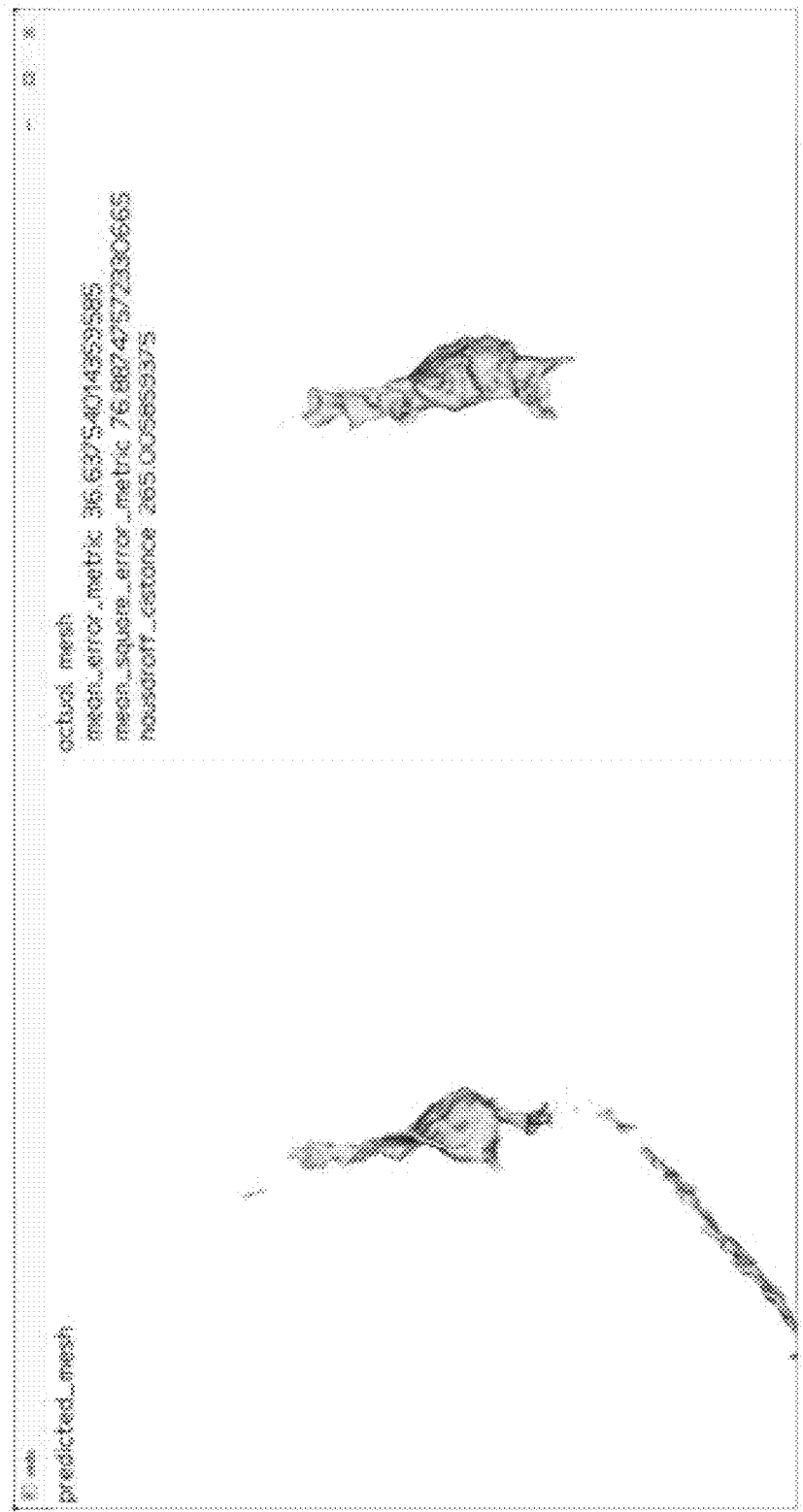
FIGS. 14A-B illustrate embodiments of mesh comparison using Impedance Data.
Figure 14B:
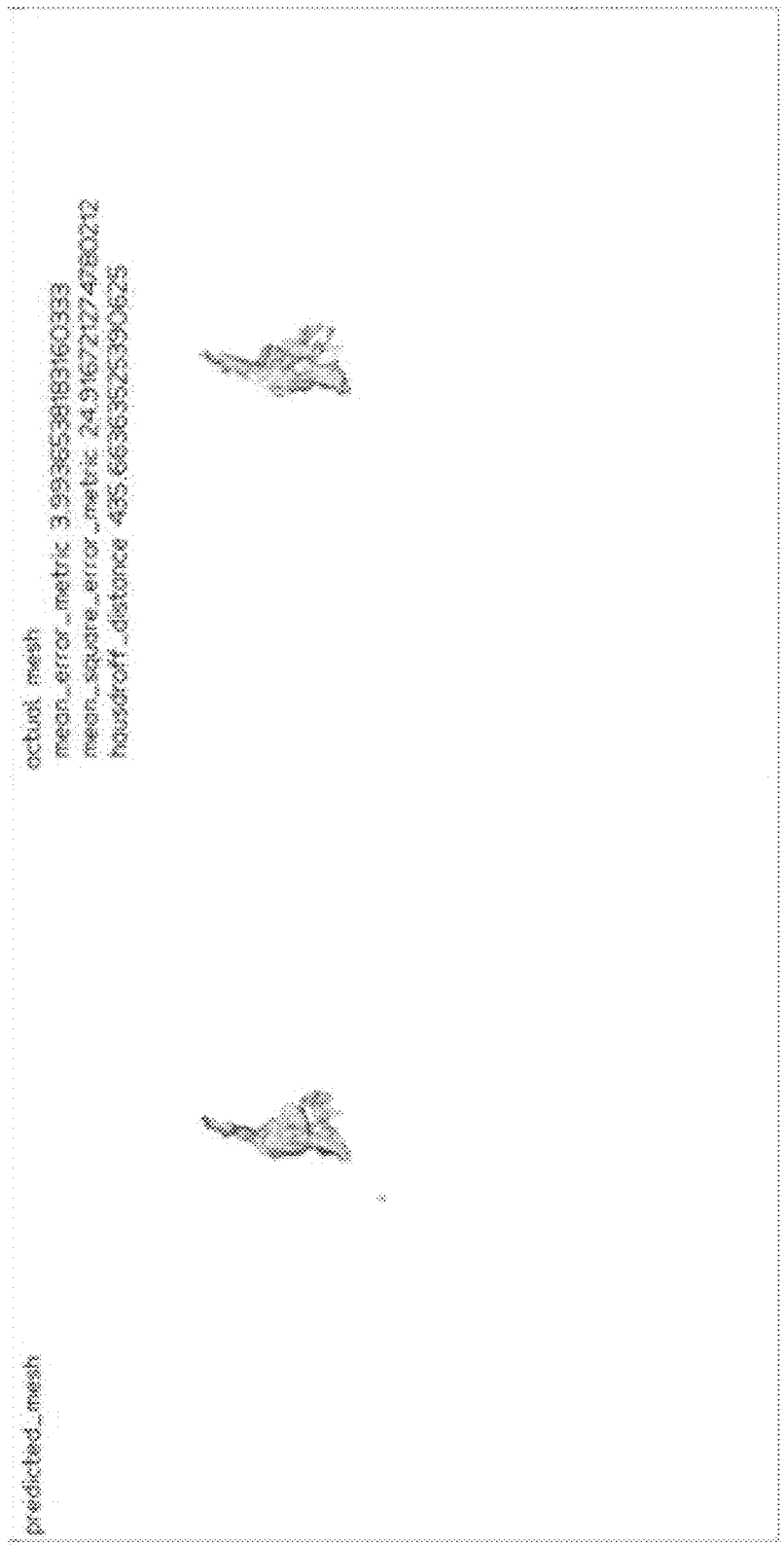

Referring now to FIG. 14A-B, illustrated is an embodiment of mesh comparison using Impedance Data. Referring to FIG. 14A, illustrated is a mesh comparison using impedance data for Run2. Referring to FIG. 14B, illustrated is a mesh comparison using impedance data for Run4. The data for Run2 and Run4 mesh comparison using impedance data is listed below:

TABLE 3

Impedance Mesh Comparison

|  | Run 2 Data | Run 4 Data |
| --- | --- | --- |
| Impedance Only | RMSE [x, y, z]: [11.57, 8.81, 19.99] mm<br>Mean RMSE: 13.45 mm<br>Mean Euclidean distance: 11.10 mm | RMSE [x, y, z]: [15.13, 6.54, 13.75] mm<br>Mean RMSE: 13.45 mm<br>Mean Euclidean distance: 14.16 mm |

The data from Run an Run may be calculated using impedance analysis, with Root Mean Square Error (RMSE) values recorded for the x, y, and z coordinates. For Run 2, the RMSE values across the axes are 11.57 mm, 8.81 mm, and 19.99 mm, respectively, resulting in a mean RMSE of 13.45 mm and a mean Euclidean distance of 11.10 mm. In Run 4, the RMSE values for x, y, and z are 15.13 mm, 6.54 mm, and 13.75 mm, leading to the same mean RMSE of 13.45 mm but a slightly higher mean Euclidean distance of 14.16 mm. These metrics indicate the variations and overall accuracy of the impedance measurements across both runs, with Run 4 showing more variability in the z-axis but similar overall error compared to Run 2.

Figure 15A:
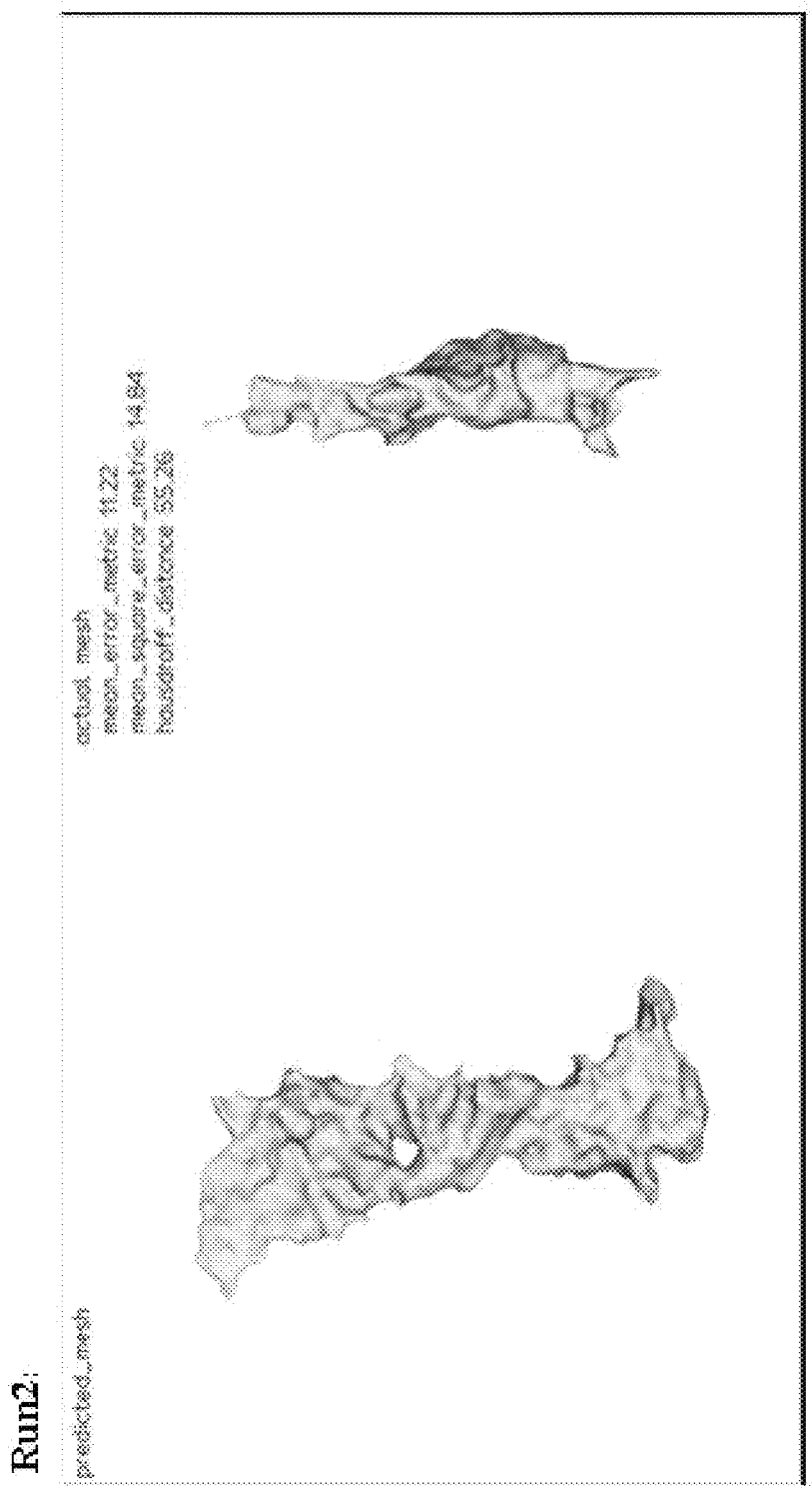
FIGS. 15A-B illustrate embodiments of mesh comparison using Impedance and Magnetic Data.
Figure 15B:
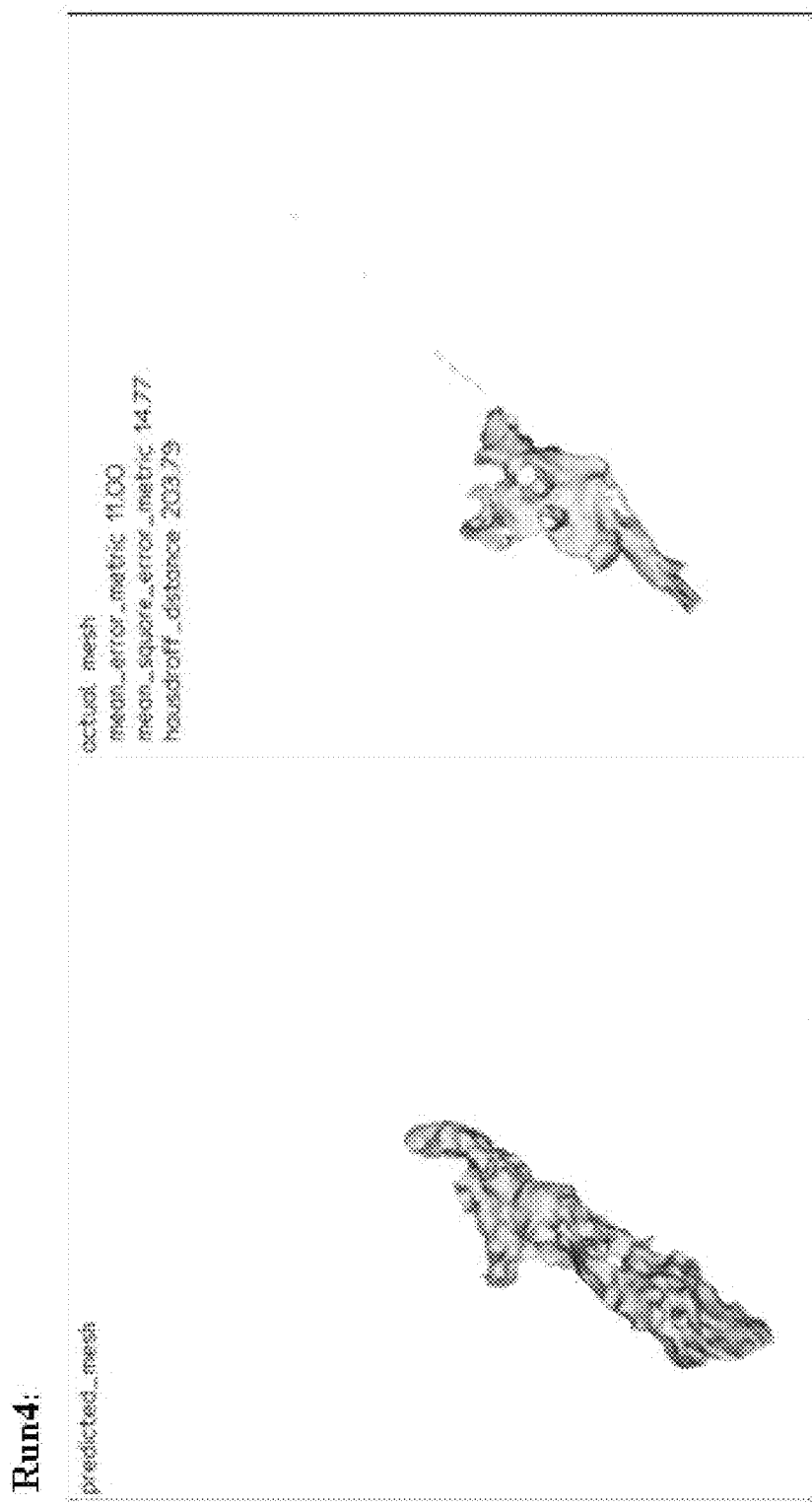

Referring now to FIG. 15A-B, illustrated is an embodiment of mesh comparison using Impedance and Magnetic Data. Referring to FIG. 15A, illustrated is a mesh comparison using impedance and magnetic data for Run2. Referring to FIG. 15B, illustrated is a mesh comparison using impedance and magnetic data for Run4. The data for Run2 and Run4 mesh comparison using impedance and magnetic data is listed below:

TABLE 4

Impedance and Magnetic Comparison

|  | Run 2 Data | Run 4 Data |
| --- | --- | --- |
| Magnetic and Impedance | RMSE [x, y, z]: [5.28, 2.67, 2.44] mm<br>Mean RMSE: 3.46 mm<br>Mean Euclidean distance: 4.86 mm | RMSE [x, y, z]: [4.65, 3.73, 6.28] mm<br>Mean RMSE: 4.88 mm<br>Mean Euclidean distance: 6.82 mm |

In Run 2, the RMSE values for the x, y, and z axes are 5.28 mm, 2.67 mm, and 2.44 mm, respectively, resulting in a mean RMSE of 3.46 mm and a mean Euclidean distance of 4.86 mm. In Run 4, the RMSE values are 4.65 mm, 3.73 mm, and 6.28 mm, with a mean RMSE of 4.88 mm and a mean Euclidean distance of 6.82 mm. These results demonstrate that the combination of magnetic and impedance data improves precision, particularly in Run 2, though Run 4 shows a slightly higher error.

Figure 16A:
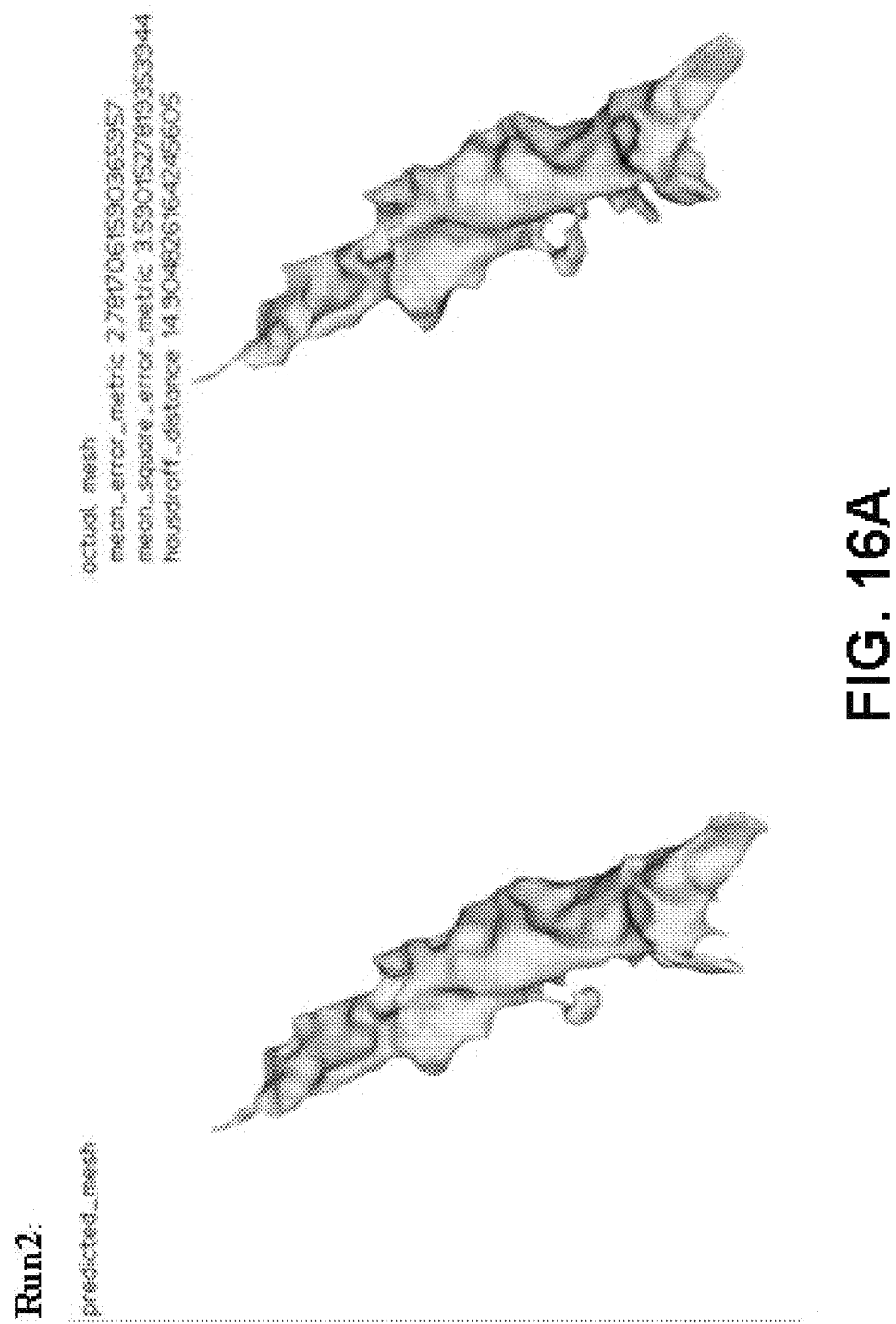
FIGS. 16A-B illustrate embodiments of mesh comparison using Impedance and Magnetic Data using a 10%-90% split fine-tuned model.
Figure 16B:
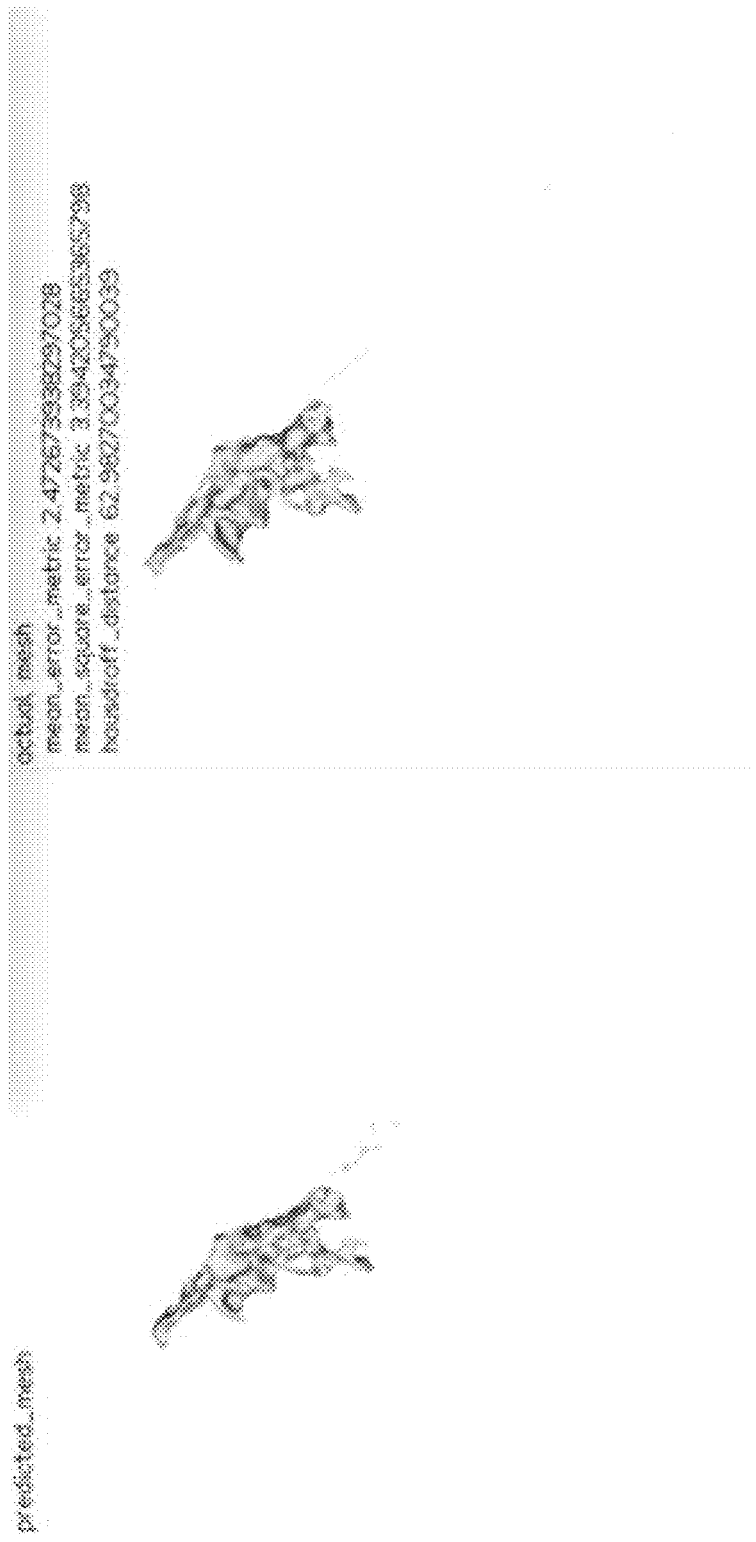

Referring now to FIG. 16A-B, illustrated is an embodiment of mesh comparison using Impedance and Magnetic Data using a 10%-90% split fine-tuned model. Referring to FIG. 16A, illustrated is a mesh comparison using impedance and magnetic data using a 10%-90% split fine-tuned model for Run2. Referring to FIG. 16B, illustrated is a mesh comparison using impedance and magnetic data using a 10%-90% split fine-tuned model for Run4. The data for Run2 and Run4 mesh comparison using impedance and magnetic data 10%-90% split fine-tuned model is listed below:

TABLE 5

Impedance and Magnetic Data using a 10%-90%
Split Fine-Tuned Model Comparison

|  | Run 2 Data | Run 4 Data |
| --- | --- | --- |
| Magnetic and Impedance Data using a 10%-90% split fine-tuned model | RMSE [x, y, z]: [1.21, 2.55, 7.43] mm<br>Mean RMSE: 3.73 mm<br>Mean Euclidean distance: 7.18 mm | RMSE [x, y, z]: [1.48, 3.12, 4.99]mm<br>Mean RMSE: 3.2 mm<br>Mean Euclidean distance: 5.28 mm |

In Run 2, the RMSE values for the x, y, and z axes are 1.21 mm, 2.55 mm, and 7.43 mm, resulting in a mean RMSE of 3.73 mm and a mean Euclidean distance of 7.18 mm. In Run 4, the RMSE values are 1.48 mm, 3.12 mm, and 4.99 mm, with a lower mean RMSE of 3.2 mm and a mean Euclidean distance of 5.28 mm. These results demonstrate that the fine-tuned model provides enhanced accuracy, especially in Run 4, where both RMSE and Euclidean distance are reduced.

Figure 17A:
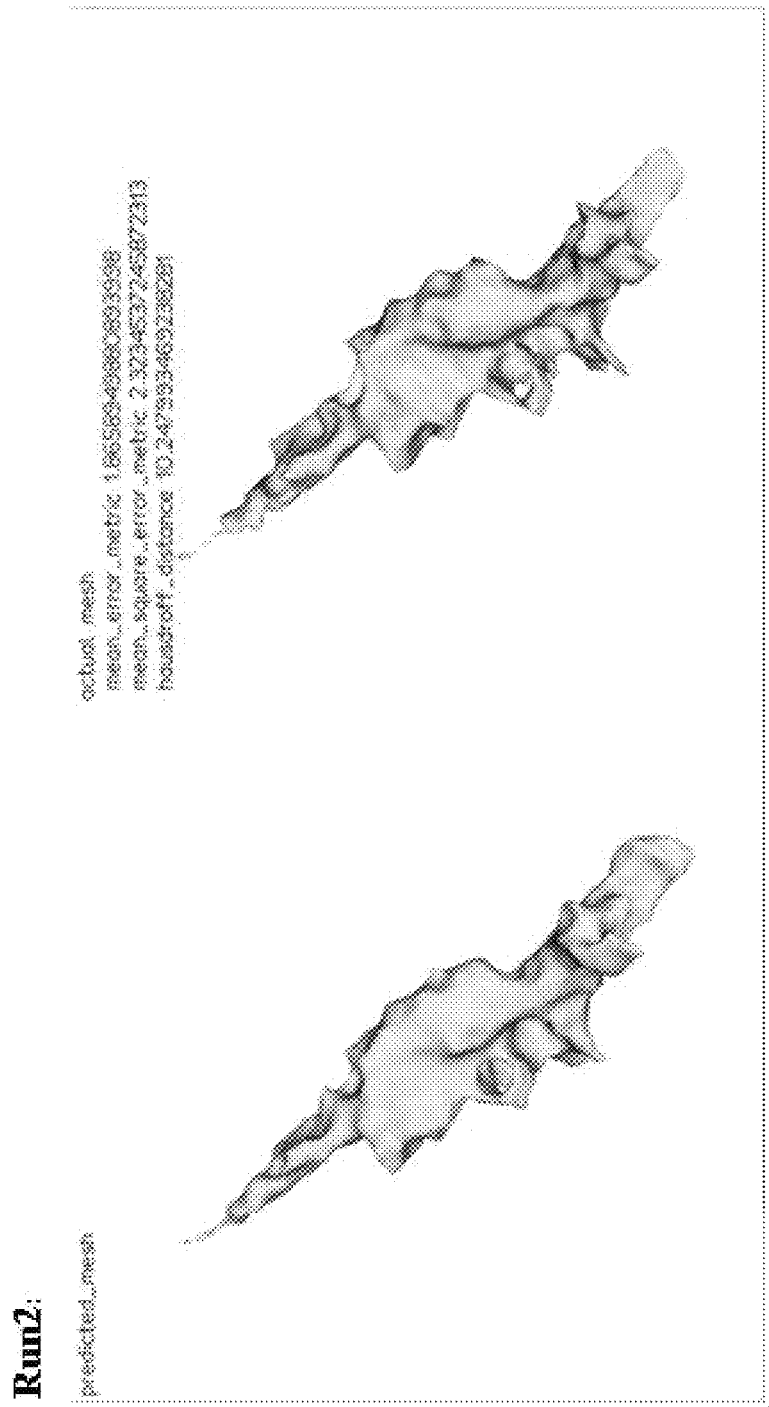
FIGS. 17A-B illustrate embodiments of mesh comparison using Impedance and Magnetic Data using a 33%-67% split fine-tuned model.
Figure 17B:
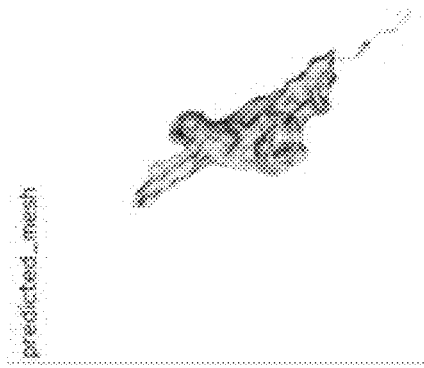

Referring now to FIG. 17A-B, illustrated is an embodiment of mesh comparison using Impedance and Magnetic Data using a 33%-67% split fine-tuned model. Referring to FIG. 17A, illustrated is a mesh comparison using impedance and magnetic data using a using a 33%-67% split fine-tuned model for Run2. Referring to FIG. 17B, illustrated is a mesh comparison using impedance and magnetic data using a using a 33%-67% split fine-tuned model for Run4. The data for Run2 and Run4 mesh comparison using impedance and magnetic data using a 33%-67% split fine-tuned model is listed below:

TABLE 6

Impedance and Magnetic Data using a 33%-67%
Split Fine-Tuned Model Comparison

|  | Run 2 Data | Run 4 Data |
| --- | --- | --- |
| Magnetic and Impedance Data using a 33%-67% split fine-tuned model | RMSE [x, y, z]: [1.21, 2.55, 7.43] mm<br>Mean RMSE: 3.73 mm<br>Mean Euclidean distance: 7.18 mm | RMSE [x, y, z]: [1.48, 3.12, 4.99]mm<br>Mean RMSE: 3.2 mm<br>Mean Euclidean distance: 5.28 mm |

In Run 2, the RMSE values for the x, y, and z axes are 2.5 mm, 3.4 mm, and 2.31 mm, resulting in a mean RMSE of 2.74 mm and a mean Euclidean distance of 4.47 mm. In Run 4, the RMSE values are 3.55 mm, 3.44 mm, and 2.70 mm, leading to a slightly higher mean RMSE of 3.23 mm and a mean Euclidean distance of 5.10 mm. These results demonstrate that the 33%-67% split fine-tuned model maintains good accuracy, with Run 2 showing lower errors, particularly in the mean Euclidean distance.

Figure 18:
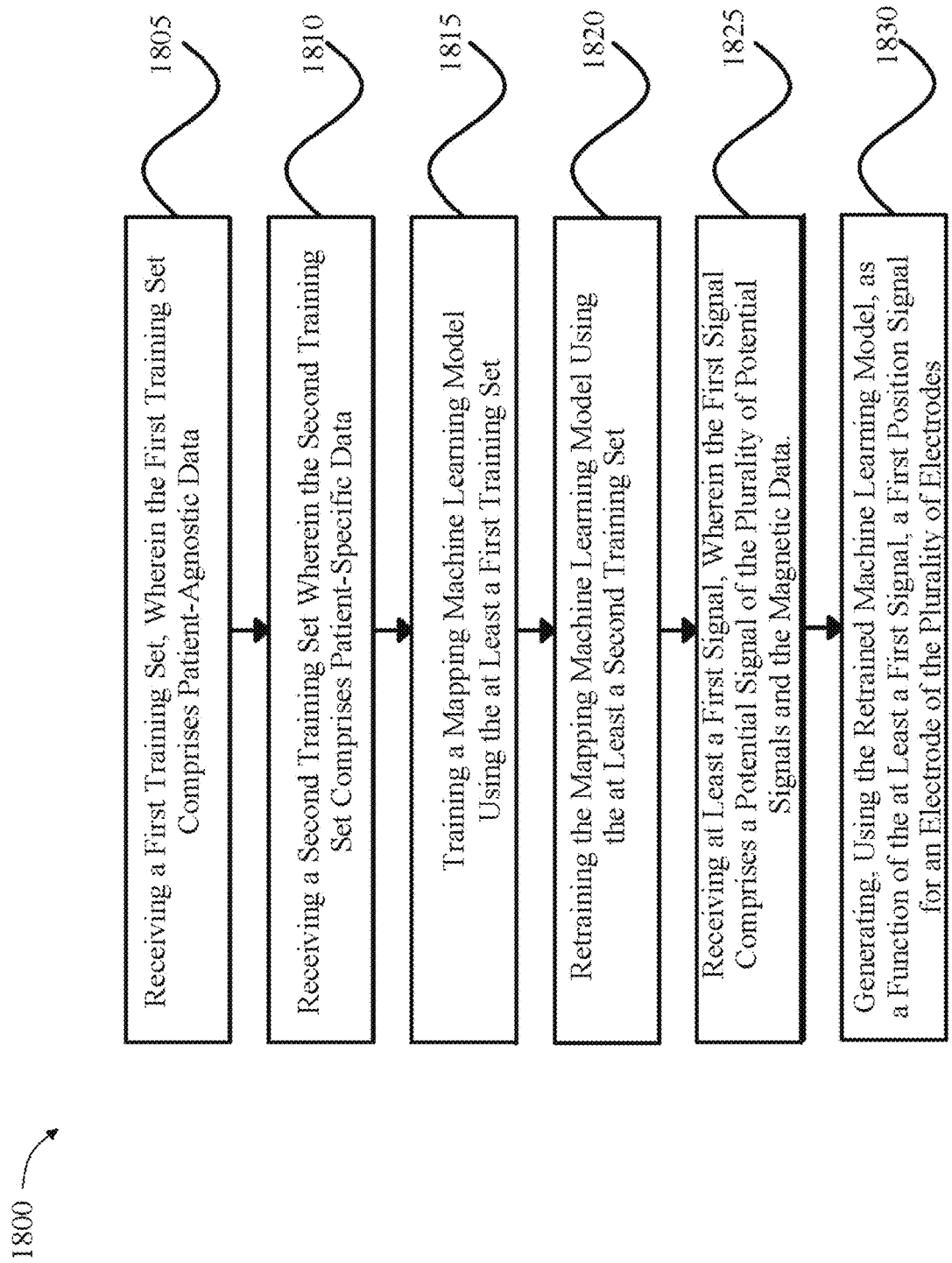
FIG. 18 is a block diagram of an exemplary embodiment of a method for determining position signals of electrodes using a retrained machine-learning model.

Referring now to FIG. 18, a flow diagram of an exemplary method 1800 for determining position signals of electrodes using a retrained machine-learning model is illustrated. At step 1805, method 1800 includes receiving, by at least a processor, a first training set, wherein the first training set comprises patient-agnostic data. This may be implemented as described and with reference to FIGS. 1-17.

Still referring to FIG. 18, at step 1810, method 1800 includes receiving, by the at least a processor, a second training set, wherein the second training set comprises patient-specific data. This may be implemented as described and with reference to FIGS. 1-17.

Still referring to FIG. 18, at step 1815, method 1800 includes training, by the at least a processor, a mapping machine-learning model using the at least a first training set. In some embodiments, the machine-learning model comprises a supervised deep learning model and the at least a first training set comprises data related to a known query electrode location on the flexible portion of the catheter. This may be implemented as described and with reference to FIGS. 1-17.

Still referring to FIG. 18, at step 1820, method 1800 includes retraining, by the at least a processor, the mapping machine-learning model using the at least a second training set. In some embodiments, wherein retraining the mapping machine-learning model using the at least a second training set comprises retraining the mapping machine-learning model using single shot learning. This may be implemented as described and with reference to FIGS. 1-17.

Still referring to FIG. 18, at step 1825, method 1800 includes receiving, by at least a catheter, at least a first signal, wherein the first signal comprises a potential signal of the plurality of potential signal and the magnetic data. In some embodiments, the plurality of electrodes comprises: a reference electrode located on a rigid portion of the catheter; and a query electrode located on a flexible portion of the catheter. In some embodiments, the plurality of electrodes comprises: a reference electrode of first electrode type; and a query electrode of second electrode type; and receiving the at least a first signal comprises: receiving a first potential signal from the reference electrode; receiving a second potential signal from the query electrode; and normalizing the second potential signal with respect to the first potential signal as a function of an electrode type transformation model. This may be implemented as described and with reference to FIGS. 1-10.

Still referring to FIG. 18, at step 1830, method 1800 includes generating, by the at least a processor, using the retrained machine-learning model, as a function of the at least a first signal, a first position signal for an electrode of the plurality of electrodes. In some embodiments, wherein the memory contains instructions further configuring the processor to validate the first position signal by generating a cross-electrode model validation, the memory contains instructions further configuring the processor to transform potential signal readings across the plurality of electrodes using the cross-electrode model validation. This may be implemented as described and with reference to FIGS. 1-10.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 19:
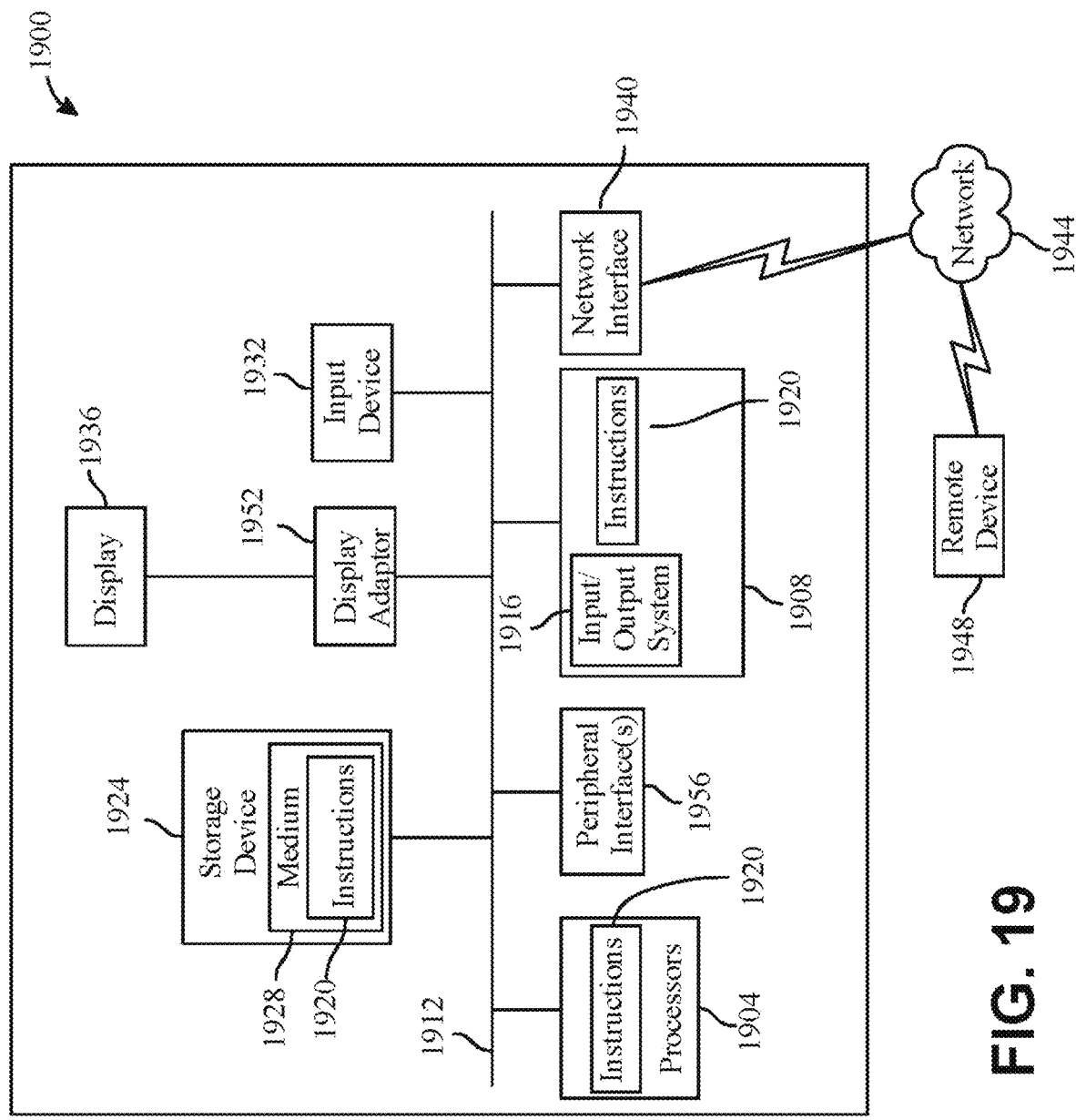
FIG. 19 is a block diagram of a computing system that can be used to implement any one or more of the methodologies disclosed herein and any one or more portions thereof.

FIG. 19 shows a diagrammatic representation of one embodiment of a computing device in the exemplary form of a computer system 1900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1900 includes a processor 1904 and a memory 1908 that communicate with each other, and with other components, via a bus 1912. Bus 1912 may include any of several types of bus structures including, but not limited to, a memory bus, a memory controller, a peripheral bus, a local bus, and any combinations thereof, using any of a variety of bus architectures.

Processor 1904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1904 may be organized according to Von Neumann and/or Harvard architecture as a non-limiting example. Processor 1904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1908 may include various components (e.g., machine-readable media) including, but not limited to, a random-access memory component, a read only component, and any combinations thereof. In one example, a basic input/output system 1916 (BIOS), including basic routines that help to transfer information between elements within computer system 1900, such as during start-up, may be stored in memory 1908. Memory 1908 may also include (e.g., stored on one or more machine-readable media) instructions (e.g., software) 1920 embodying any one or more of the aspects and/or methodologies of the present disclosure. In another example, memory 1908 may further include any number of program modules including, but not limited to, an operating system, one or more application programs, other program modules, program data, and any combinations thereof.

Computer system 1900 may also include a storage device 1924. Examples of a storage device (e.g., storage device 1924) include, but are not limited to, a hard disk drive, a magnetic disk drive, an optical disc drive in combination with an optical medium, a solid-state memory device, and any combinations thereof. Storage device 1924 may be connected to bus 1912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1924 (or one or more components thereof) may be removably interfaced with computer system 1900 (e.g., via an external port connector (not shown)). Particularly, storage device 1924 and an associated machine-readable medium 1928 may provide nonvolatile and/or volatile storage of machine-readable instructions, data structures, program modules, and/or other data for computer system 1900. In one example, software 1920 may reside, completely or partially, within machine-readable medium 1928. In another example, software 1920 may reside, completely or partially, within processor 1904.

Computer system 1900 may also include an input device 1932. In one example, a user of computer system 1900 may enter commands and/or other information into computer system 1900 via input device 1932. Examples of an input device 1932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1932 may be interfaced to bus 1912 via any of a variety of interfaces (not shown) including, but not limited to, a serial interface, a parallel interface, a game port, a USB interface, a FIREWIRE interface, a direct interface to bus 1912, and any combinations thereof. Input device 1932 may include a touch screen interface that may be a part of or separate from display 1936, discussed further below. Input device 1932 may be utilized as a user selection device for selecting one or more graphical representations in a graphical interface as described above.

A user may also input commands and/or other information to computer system 1900 via storage device 1924 (e.g., a removable disk drive, a flash drive, etc.) and/or network interface device 1940. A network interface device, such as network interface device 1940, may be utilized for connecting computer system 1900 to one or more of a variety of networks, such as network 1944, and one or more remote devices 1948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1944, may employ a wired and/or a wireless mode of communication. In general, any network topology may be used. Information (e.g., data, software 1920, etc.) may be communicated to and/or from computer system 1900 via network interface device 1940.

Computer system 1900 may further include a video display adapter 1952 for communicating a displayable image to a display device, such as display device 1936. Examples of a display device include, but are not limited to, a liquid crystal display (LCD), a cathode ray tube (CRT), a plasma display, a light emitting diode (LED) display, and any combinations thereof. Display adapter 1952 and display device 1936 may be utilized in combination with processor 1904 to provide graphical representations of aspects of the present disclosure. In addition to a display device, computer system 1900 may include one or more other peripheral output devices including, but not limited to, an audio speaker, a printer, and any combinations thereof. Such peripheral output devices may be connected to bus 1912 via a peripheral interface 1956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for determining position signals of electrodes using a retrained machine-learning model, the system comprising:
   at least a catheter comprising:
      a plurality of electrodes configured to collect a plurality of potential signals; and
      a magnetic sensor configured to collect magnetic data; and
   at least a computing device, wherein the computing device comprises:
      a memory; and
      at least a processor connected to the memory, wherein the memory contains instructions configuring the at least a processor to:
         receive a first training set, wherein the first training set comprises patient-agnostic data;
         receive a second training set, wherein the second training set comprises patient-specific data;
         train a mapping machine-learning model using the first training set, wherein the mapping machine-learning model is configured to determine position signals for electrodes as a function of magnetic information and potential signals;
         determine an accuracy score of the mapping machine-learning model based on a plurality of cohort feedback;
         retrain the mapping machine-learning model based on the accuracy score using the second training set;
         receive at least a first signal, wherein the first signal comprises a potential signal of the plurality of potential signals and the magnetic data; and
         generate, using the retrained mapping machine-learning model, as a function of the at least a first signal, a first position signal for an electrode of the plurality of electrodes;
         evaluate the retrained machine-learning model using point-wise system configured to analyze an accuracy of predicted positions or signals by evaluating an error between a true and predicted points in three-dimensional space.

2. The system of claim 1, wherein:
   the plurality of electrodes comprises:
      a reference electrode located on a rigid portion of the catheter; and
      a query electrode located on a flexible portion of the catheter; and
   the first position signal is for the query electrode.

3. The system of claim 1, wherein the mapping machine-learning model comprises a supervised deep learning model.

4. The system of claim 1, wherein the memory contains instructions further configuring the processor to validate the first position signal by generating a cross-electrode model validation.

5. The system of claim 1, wherein a location of the plurality of electrodes is computed as a function of at least the magnetic sensor and rigid inter-electrode distances.

6. The system of claim 1, wherein retraining the mapping machine-learning model using the at least a second training set comprises retraining the mapping machine-learning model using single shot learning.

7. The system of claim 1, wherein:
   the plurality of electrodes comprises:
      a reference electrode of first electrode type; and
      a query electrode of second electrode type; and
   receiving the at least a first signal comprises:
      receiving a first potential signal from the reference electrode;
      receiving a second potential signal from the query electrode; and
      normalizing the second potential signal with respect to the first potential signal as a function of an electrode-type transformation model.

8. The system of claim 1, wherein the at least a first training set comprises exemplary magnetic data, exemplary reference electrode potential signals, exemplary reference electrode position signals, and exemplary query electrode potential signals correlated to exemplary query electrode position signals.

9. The system of claim 4, wherein the memory contains instructions further configuring the processor to transform potential signal readings across the plurality of electrodes using the cross-electrode model validation.

10. The system of claim 7, wherein the electrode-type transformation model is a machine-learning model trained using training data correlating potential readings from the first electrode type to potential readings from the second electrode type.

11. A method for determining position signals of electrodes using a retrained machine-learning model, the method comprising:
   receiving, by at least a processor, a first training set, wherein the first training set comprises patient-agnostic data;
   receiving, by the at least a processor, a second training set, wherein the second training set comprises patient-specific data;
   training, by the at least a processor, a mapping machine-learning model using the first training set, wherein the mapping machine-learning model is configured to determine position signals for electrodes as a function of magnetic information and potential signals;
   determine an accuracy score of the mapping machine-learning model based on a plurality of cohort feedback;
   retraining, by the at least a processor based on the accuracy score, the mapping machine-learning model using the at least a second training set;
   receiving, by at least a catheter, at least a first signal, wherein the first signal comprises a potential signal of a plurality of potential signals and the magnetic data; and
   generating, by the at least a processor, using the retrained machine-learning model, as a function of the at least a first signal, a first position signal for an electrode of the plurality of electrodes;
   evaluating, by the at least a processor, the retrained machine-learning model using point-wise system configured to analyze an accuracy of predicted positions or signals by evaluating an error between a true and predicted points in three-dimensional space.

12. The method of claim 11, wherein:
the plurality of electrodes comprises:
   a reference electrode located on a rigid portion of the catheter; and
   a query electrode located on a flexible portion of the catheter; and
the first position signal is for the query electrode.

13. The method of claim 11, wherein the mapping machine-learning model comprises a supervised deep learning model.

14. The method of claim 11, further comprising, validating, by the at least a processor, the first position signal by generating a cross-electrode model validation.

15. The method of claim 11, wherein a location of the plurality of electrodes is computed as a function of at least a magnetic sensor and rigid inter-electrode distances.

16. The method of claim 11, wherein retraining the mapping machine-learning model using the at least a second training set comprises retraining the mapping machine-learning model using single shot learning.

17. The method of claim 11, wherein:
the plurality of electrodes comprises:
   a reference electrode of first electrode type; and
   a query electrode of second electrode type; and
receiving the at least a first signal comprises:
   receiving a first potential signal from the reference electrode;
   receiving a second potential signal from the query electrode; and
   normalizing the second potential signal with respect to the first potential signal as a function of an electrode type transformation model.

18. The method of claim 11, wherein the at least a first training set comprises exemplary magnetic data, exemplary reference electrode potential signals, exemplary reference electrode position signals, and exemplary query electrode potential signals.

19. The method of claim 14, further comprising, transforming, by the at least a processor, potential signal readings across the plurality of electrodes using the cross-electrode model validation.

20. The method of claim 17, wherein the electrode type transformation model is a machine-learning model trained using training data correlating potential readings from the first electrode type to potential readings from the second electrode type.

* * * * *